(12) United States Patent
Reisinger et al.

US009593319B2

(10) Patent No.: US 9,593,319 B2
(45) Date of Patent: Mar. 14, 2017

(54) TEMPERATURE-STABLE β-PYRANOSIDASE

(75) Inventors: Christoph Reisinger, Munich (DE); Farah Qoura, Munich (DE); Barbara Klippel, Hamburg (DE); Garabed Antranikian, Hittfeld-Waldesruh (DE)

(73) Assignee: CLARIANT PRODUKTE (DEUTSCHLAND) GMBH, Frankfurt am Main (DE)

( * ) Notice: Subject to any disclaimer, the term of this patent is extended or adjusted under 35 U.S.C. 154(b) by 108 days.

(21) Appl. No.: 13/881,882

(22) PCT Filed: Oct. 26, 2011

(86) PCT No.: PCT/EP2011/068734
§ 371 (c)(1),
(2), (4) Date: Jul. 29, 2013

(87) PCT Pub. No.: WO2012/055904
PCT Pub. Date: May 3, 2012

(65) Prior Publication Data
US 2013/0330784 A1    Dec. 12, 2013

(30) Foreign Application Priority Data
Oct. 26, 2010  (DE) .................. 10 2010 042 910

(51) Int. Cl.
| *C12N 1/21* | (2006.01) |
| *C12N 9/42* | (2006.01) |
| *C12N 15/56* | (2006.01) |
| *C12N 15/62* | (2006.01) |
| *C07K 19/00* | (2006.01) |
| *C12N 9/24* | (2006.01) |
| *C12N 15/52* | (2006.01) |

(52) U.S. Cl.
CPC ............ *C12N 9/2402* (2013.01); *C12N 9/248* (2013.01); *C12N 9/2437* (2013.01); *C07K 2319/02* (2013.01); *C07K 2319/20* (2013.01); *C12N 15/52* (2013.01); *C12N 15/62* (2013.01)

(58) Field of Classification Search
None
See application file for complete search history.

(56) References Cited

FOREIGN PATENT DOCUMENTS

| WO | WO-2009/094187 A1 | 7/2009 |
| WO | WO-2009/146464 A2 | 12/2009 |

OTHER PUBLICATIONS

Varghese, et al., "Three-dimensional Structure of a Barley Beta-D-Glucan Exohydrolase, a Family 3 Glycosyl Hydrolase", *Structure*, vol. 7, No. 2, p. 179-190, Feb. 1999.
Henrissat, B., et al., "A Scheme for Designating Enzymes that Hydrolyse the Polysaccharides in the Cell Walls of Plants", FEBS Letters, vol. 425, No. 2, p. 352-354, Mar. 1998.
Andrews, et al., "*Fervidobacterium Godwanese* sp. *nov.*, A New Thermophyllic Anaerobic Bacterium Isolated from Nonvolcanically Heated Geothermal Waters of the Great Artesian Basin of Australia", *International Journal of Systematic Bacteriology*, vol. 46, No. 1, p. 265-269, Jan. 1996.
Database UniProt [Online], Nov. 13, 2007 (Nov. 13, 2007), "SubName:Full=Glycoside hydrolase family 3 domain protein", XP002667902, retrieved from EBA accession No. UNIPROT:A8F439, Database accession No. A8F439 sequence.
International Search Report for PCT/EP2011/068734 mailed Feb. 8, 2012.

*Primary Examiner* — Robert Mondesi
*Assistant Examiner* — Todd M Epstein
(74) *Attorney, Agent, or Firm* — Gianna Julian-Arnold; Saul Ewing LLP

(57) ABSTRACT

The invention relates to temperature-stable polypeptides with β-pyranosidase activity. The polypeptide substrates include β-glucopyranosides and β-xylopyranosides. The polypeptides can be expressed alone or as fusion proteins for example in yeast or bacteria and subsequently purified. The polypeptides according to the invention can be used alone or in a mixture with other enzymes for the degradation of plant raw materials, among others for the enzymatic degradation of biomass containing lignocellulose, in particular hemicellulose and the hemicellulose component xylan. The enzymes are suitable for use in textile processing, as an additive of detergents, or in the food or feed industry.

11 Claims, 12 Drawing Sheets

TEMPERATURE-STABLE β-PYRANOSIDASE

RELATED APPLICATIONS

Figure 1:
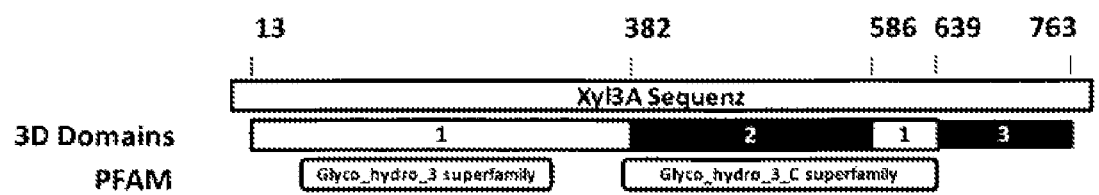

This application is a 35 U.S.C. §371 national stage filing of International Application No. PCT/EP2011/068734, filed Oct. 26, 2011, which is related and claims priority to DE Application Serial No.: 10 2010 042 910.4, filed Oct. 26, 2010. The entire contents of these applications are explicitly incorporated herein by reference.

BACKGROUND

In view of the decreasing supply of fossil fuels and increasing $CO_2$ emissions, the exploitation of renewable biomass of plant origin as an alternative source of energy is becoming increasingly important. As a result of the continuously increasing and greatly accelerating demand for energy by industrialised and emerging countries, equivalent alternative energy sources need to be found in addition to a more efficient utilisation of fossil energy supplies (Lyco et al., 2009, J. Biotechnol. 142 (1): 78-86).

The focus of research is shifting to the concept of bio-refining where biomass of plant origin is used as a source of both energy and raw materials. The objective of bio-refining is the full use of renewable raw materials for the production of chemicals, fuels and energy. Dry biomass such as straw and wood obtained from raw and waste materials containing lignocellulose is used as the starting material of lignocellulose bio-refining.

Special interest is dedicated to the utilisation of raw materials containing lignocellulose which originate from agriculture and forestry residues such as straw and wood as these are inexpensive and do not compete with the food and feed industry (Lyco et al., 2009, J. Biotechnol. 142 (1): 78-86; Kumar et al., 2008, J. Ind. Microbiol. Biotechnol. 35 (5): 377-391; Peters, 2007, Adv. Biochem. Eng. Biotechnol. 105: 1-30; Kamm et al., 2006, Biochem. Mol. Biol. Int. 44 (2): 283-292). Lignocellulose is the biopolymer which is available in the largest quantities on earth and consists of cellulose, hemicellulose and lignin. The proportion of cellulose is about 30-60%, that of hemicellulose about 20-40% and the lignin proportion is about 10-30%. In contrast to cellulose which is composed of unbranched glucose units, hemicellulose consists of pentoses and hexoses which may have additional carbohydrate branches. Lignin, on the other hand, is a polymer of phenolic molecules (Peters, 2007, Adv. Biochem. Eng. Biotechnol. 105: 1-30).

The use of lignocellulose in bio-refining requires reacting the raw material to obtain useful sugars. For this purpose, lignocellulose is pre-treated by mechanical, thermal and/or chemical methods so as to make the cellulose and hemicellulose more accessible for subsequent hydrolysis (Hendriks & Zeeman, 2009, Bioresour. Technol. 100 (1): 10-18). In enzymatic hydrolysis, especially cellulolytic and xylanolytic enzymes play a critical role. These enzymes which belong to the glycoside hydrolases are capable of decomposing the glycosidic bonds in cellulose and hemicellulose.

In addition to the use of cellulolytic and xylanolytic enzymes of mesophilic micro-organisms, the use of thermostable enzymes is of increasing interest as they are suitable for high-temperature processes which increases both the solubility and hence accessibility of the substrate (Turner et al., 2007, Microb. Cell. Fact. 6: 9). Moreover, thermostable enzymes are characterised by increased specificity of the substrate and stability vis-àvis solvents and detergents (Viikari et al., 2007, Adv. Biochem. Eng. Biotechnol. 108: 121-145; Antranikian G. (2008) in: Industrial relevance of thermophiles and their enzymes—Thermophiles—Biology and Technology at High Temperatures, ed. Robb Fea (CRC Press, Taylor & Francis, Boca Raton), pp 113-160).

Xylan

Xylan, the second-most frequent polysaccharide in nature, is the main component of hemicellulose. It is arranged within the fibril between cellulose and lignin and plays an important role in keeping the micro-fibrils together. Xylans consist of a homopolymer backbone of β-1,4-linked xylopyranose units. This is either linear and unsubstituted, may additionally be acetylated or substituted with arabinosyl and glucuronopyranosyl groups. Therefore, a distinction is made between homoxylan, arabinoxylan, glucuronoxylan and glucuronoarabinoxylan (Saha, 2003, J. Ind. Microbiol. Biotechnol. 30 (5): 279-291; Bergquist et al., 2001, Methods Enzymol 330: 301-319; Kulkarni et al., 1999, FEMS Microbiol. Rev. 23 (4): 411-456). In most cases, xylans are present as complex, highly branched heteropolymers (Collins et al., 2002).

The full hydrolysis of xylans to obtain monosaccharides requires a plurality of enzymes which jointly contribute to degradation (Collins et al., 2005, FEMS Microbiol. Rev. 29 (1): 3-23; Bergquist et al., 2001, Methods Enzymol 330: 301-319). Endoxylanases cleave the glycosidic bonds within the xylan backbone, mainly forming shorter xylol oligosaccharides, but also xylose, xylobiose and xylotriose (Polizeli et al. 2005, Appl. Microbiol. Biotechnol. 67 (5): 577-591; Dwivedi et al., 1996, Appl. Microbiol. Biotechnol. 45 (1-2): 86-93). Xylosidases cleave off xylose monomers from the non-reducing end of xylooligosaccharides and xylobiose, whereas xylan is generally not used as a substrate (Collins et al., 2005, FEMS Microbiol. Rev. 29 (1): 3-23; Polizeli et al., 2005, Appl. Microbiol. Biotechnol. 67 (5): 577-591). Additional enzymes such as α-arabinofuranosidases, α-glucuronidases and acetyl xylan esterases are involved in the release of side groups of heterogeneous xylans. α-Arabinofuranosidases separate arabinose from branched arabinoxylans and arabinans, while α-glucuronidases hydrolyse the α-1,2 bonds between the β-xylopyranosyl backbone and the glucuronic acid. Acetylated xylan is hydrolysed by acetyl xylan esterases which separate the acetyl groups of the xylan (Jaeger et al., 2006, Biokatalyse. Angewandte Mikrobiologie, ed. Antranikian G. Springer Verlag, pp 135-160). Xylanolytic enzymes have been identified both in fungi and bacteria and in archaea.

Glycoside Hydrolases

Glycoside hydrolases are enzymes which hydrolyse the glycosidic bonds between one or more carbohydrates and a residue that does not contain carbohydrates. They cleave a plurality of α- and β-linked substrates and are distinguished in terms of their substrate specificity. Glycoside hydrolases are classified on the basis of similarities of the amino acid sequence or, respectively, percentage identities of the amino acid sequence into so-called glycosidehydrolase families (GH families). In addition to a similar amino acid sequence, the members of a family have a similar three-dimensional structure and the same reaction mechanism (Henrissat, 1991, Biochem. J. 280 (Pt 2): 309-316).

A list of the GH families may be found in the CAZy data base ("Carbohydrate-Active enZymes") in the Internet (Cantarel et al., 2009). Glycoside hydrolases are divided into two classes according to their reaction mechanism: (1) into enzymes which cleave the glycosidic bonds with reversal of the configuration of the anomeric carbon atom and (2) into enzymes which hydrolyse the glycosidic bonds while maintaining the anomeric configuration (Davies & Henrissat, 1995, Structure 3 (9): 853-859; McCarter & Withers, 1994, Curr. Opin. Struct Biol 4 (6): 885-892). Aspartate and/or glutamate residues have been identified as catalytic amino acids in most glycoside hydrolases; however other amino acid residues may also be involved in cleaving the glycosidic bond (Davies & Henrissat, 1995, Structure 3 (9):853-859).

Glycoside hydrolases consist of a catalytic domain and may contain additional domains binding carbohydrates. This are connected to the catalytic domain by a flexible linker and permit the enzymes to bind to the substrate (Shoseyov et al., 2006; Boraston et al., 2004, Biochem. J. 382 (Pt 3): 769-781). The nomenclature for glycoside hydrolases has been standardised by Henrissat et al. (1998, FEBS Lett. 425 (2): 352-354).

Thus the designation of the enzymes and the genes encoding them is made by indicating the substrate in the form of three letters. The designation for the substrate is followed by the number of the GH family the enzyme belongs to and a letter indicating the order in which the enzymes have been identified. An abbreviation for the species is placed first so as to distinguish similar enzymes of different organisms.

Endoxylanases of Thermophilic Bacteria

A number of endoxylanases of thermophilic bacteria are known which are classified into the glycoside hydrolase families 10, 11 and 43 according to Henrissat et al. (1998, FEBS Lett. 425 (2): 352-354), owing to similarities of the amino acid sequences. Bacteria of the species *Caldicellulosiruptor* produce endoxylanases with maximum activities at temperatures of 65-70° C. and pH 5.5-6.5. Many endoxylanases are also formed by the anaerobic bacterium *Clostridium*.

In addition to the endoxylanase activity, the enzymes XynC and XynX of *C. thermocellum* display the activity of an endoglucanase (Jung et al., 1998, Biochem. Mol. Biol. Int. 44 (2): 283-292; Hayashi et al., 1997, J. Bacteriol. 179 (13): 4246-4253). The endoxylanases XynC and XynY are known to be located in cellulosomes (Hayashi et al., 1997, J. Bacteriol. 179 (13): 4246-4253; Fontes et al., 1995, Biochem. J. 307 (Pt 1): 151-158).

The most thermo-stable endoxylanases are produced by *Thermotoga maritima* and *T. neapolitana*. These show maximum activities at 85-105° C. and half-lives of up to 22 hrs at 90° C. and, respectively, 12 hrs at 95° C. (Zverlov et al., 1996 Appl. Microbiol. Biotechnol. 45 (1-2): 245-247; Saul et al., 1995, Appl. Environ. Microbiol. 61 (11): 4110-4113; Winterhalter & Liebl, 1995, Appl. Environ. Microbiol. 61 (5): 1810-1815). Additional endoxylanases are formed of thermophilic bacteria from the species *Geobacillus, Rhodothermus, Thermoanaerobacterium* and *Thermobifida*.

β-Xylosidases of Thermophilic Bacteria

The β-xylosidases known to date are formed by thermophilic bacteria of the genera *Caldicellulosiruptor, Clostridium, Geobacillus, Thermoanaerobacter* and *Thermoanaerobacterium*. They are classified into glycoside hydrolase families 3, 39, 43 and 52 according to Henrissat et al. (1998, FEBS Lett. 425 (2): 352-354) on the basis of similarities of the amino acid sequences. In addition to β-xylosidases, the anaerobic bacterium *Clostridium stercorarium* also produces endoxylanases and α-arabinofuranosidases and is hence capable of fully degrading arabinoxylan to obtain xylose and arabinan (Adelsberger et al., 2004, Microbiology 150 (Pt 7): 2257-2266).

The gene encoding the β-xylosidase XynB1 of *G. stearothermophilus* is part of a gene cluster which encodes other enzymes involved in the degradation of xylan. In addition to the gene for the β-xylosidase XynB1, this cluster also contains genes for xylanases and α-glucuronidases (Shulami et al., 1999, J. Bacteriol. 181 (12): 3695-3704). The genes encoding the β-xylosidases of *Thermo anaerobacter brockii* and *Thermoanaerobacterium* sp. JW/SL YS485 are also located directly beside genes encoding a β-glucosidase or, respectively, an acetyl xylan esterase (Breves et al., 1997, Appl. Environ. Microbiol. 63 (10): 3902-3910; Lorenz & Wiegel, 1997, J. Bacteriol. 179(17): 5436-5441).

Industrial Applications of Cellulolytic and Xylanolytic Enzymes

The use of cellulolytic and xylanolytic is widespread in the industry. For example, they are used in food and feed production, but cellulases and xylanases are also employed in the paper, pulp and in the textile industry. Their use serves the purpose of increasing yield and improving quality. Moreover, the enzymes are used as an environmentally harmless alternative to conventional methods of treatment.

In the food industry, the cellulolytic and xylanolytic enzymes are used for preparing fruit juices, wine and beer, and in the extraction of oil, preferably olive oil, rapeseed oil and sunflower oil as well as in the baked goods industry. In the preparation of fruit juices, cellulases and hemicellulases are used together with pectinases to increase the yield of the juice and to clarify fruit juices. By treating the flesh of fruit with the enzymes, the formation of juice is enhanced and simultaneously the process time is shortened. By subsequently clarifying the juice with the aid of the enzymes, the viscosity is reduced and the filterability thus improved. However, cellulases and hemicellulases are also used together with pectinases in the preparation of oil, preferably olive oil, rapeseed oil and sunflower oil in order to enhance extraction. These enzymes are also used in the preparation of wines where they contribute to clarification, but also to the extraction of dyes present in the fruit and to improving the aroma of the wine.

Moreover, cellulases are used in breweries to hydrolyse barley glucan so as to facilitate filtration of the beer. Xylanases are also used in the baked goods industry. There, they are used as a flour additive to make the dough easier to process and improve the quality of the baked goods (Beg et al., 2001, Appl. Microbiol. Biotechnol. 56 (3-4): 326-338; Bhat, 2000, Biotechnol. Adv. 18 (5): 355-383; Galante et al., 1998, in: Enzymes, biological control and commercial applications, eds. Harman G E & Kubicek C P, publisher Taylor & Francis, London, Vol. 2, pp. 327-342; Bhat & Bhat, 1997, Biotechnol. Adv. 15 (3-4): 583-620).

Cellulases and xylanases are also used in the feed industry where the enzymes contribute to an increase of the nutritional value and easier digestibility of the feed by digesting the cellulose and hemicellulose in feed products of plant origin (Bhat & Bhat, 1997, Biotechnol. Adv. 15 (3-4): 583-620).

In the paper and pulp industry, cellulases and xylanases are used to modify the wood fibre structure so as to make the pulp easier to process. However, the use of xylanases for bleaching paper is also widespread. In such applications, treatment of the pulp with endoxylanases results in the release of lignin, thus rendering the cell wall of the wood fibres more accessible for bleaching agents, whereby the use of bleaching agents can be significantly reduced (Bhat, 2000, Biotechnol. Adv. 18 (5): 355-383; Buchert et al., 1998, in: *Trichoderma & Gliocladium*—enzymes, biological control and commercial applications, eds. Harman G E & Kubicek C P, publisher Taylor & Francis, London, Vol. 2, pp 343-363).

DISCLOSURE OF THE INVENTION

Definitions

The term "glycoside hydrolase" refers to a protein with enzymatic activity which is capable of hydrolysing glycosidic bonds between carbohydrates or between a carbohydrate and a residue that does not contain a carbohydrate.

The term "β-pyranosidase" refers to a glycoside hydrolase having the activity of a β-glycosidase (E.G. 3.2.1.-) which is capable of catalysing the hydrolysis of a β-glycosidic bond on a pyranose.

The terms "β-glucopyranosidase" and "β-glucosidase" refer to a glycoside hydrolase which is capable of catalysing the hydrolysis of a β-glycosidic bond on a glucose, producing low-molecular glucose oligomers or monomers.

The terms "β-xylopyranosidase" and "β-xylosidase" refer to a glycoside hydrolase which is capable of catalysing the hydrolysis of a β-glycosidic bond on a xylose, producing low-molecular xylose oligomers or monomers.

A "polypeptide" is an oligomer or polymer of amino acid elements which are linked to each other by peptide bonds.

The term "monomer or oligomer component" includes all monomer or oligomer components which may be released from a polymer by enzymatic activity. The term oligomer includes all compounds of at least two components.

"Family 3 glycoside hydrolase" or "glycoside hydrolase of family 3" refers to a polypeptide having glycoside hydrolase activity which is assigned to family 3 according to Henrissat et al. (1998, FEBS Lett. 425 (2): 352-354).

"Structural domain 1" of glycoside hydrolase 3 refers to a domain which has at least 50%, preferably at least 70%, and more preferably at least 90% identity of the amino acid sequence with the sequence section comprising amino acid residues 1 to 357 of SEQ ID NO. 4 (barley β-D-glucan exohydrolase isoenzyme Exo I, gene bank reference number AF102868.1, published in: Varghese et al., 1999, Structure, Vol. 7, No. 2, p 179-190).

"Structural domain 2" of glycoside hydrolase 3 refers to a domain having at least 50%, preferably at least 70% and more preferably at least 90% identity of the amino acid sequence with the sequence section comprising the amino acid residues 374 to 559 of SEQ ID. NO. 4 (barley β-D-glucan exohydrolase isoenzyme Exo I, Varghese et al., 1999, Structure, Vol. 7, No. 2, p 179-190).

The term "% identity" in relation to amino acid or nucleotide sequences means the percentage determined by using the following method: The alignment of two aminco acid sequences with each other or two nucleic acid sequences with each other is carried out with AlignX. AlignX is a stand-alone application sold by Invitrogen with Vector NTI Advance 10.3.0. The algorithm for the alignments is the ClustalW algorithm (Nucleic Acid Research, 22 (22): 4673-4680, 1994). The parameters used are the value 15/10 for the gap opening penalty and value 6.66/0.1 for the gap extension penalty.

"Similar sequences" are characterised by certain minimum percentage identities among each other, expressed by a number value, for example at least 30%, at least 50%, at least 70% or at least 90%, and refer to sequences or sequence sections the common evolutionary origin of which may be detected by other criteria such as structural comparisons.

The term "mutation" comprises any kind of nucleotide sequence modification or amino acid sequence modification including deletions, insertions, point mutations, inversions of combinations thereof.

"pNP" represents para-nitrophenyl.

"Thermostability" or "temperature stability" relates to a characteristic of an enzyme which may be determined by dividing an enzyme preparation into two fractions one of which is exposed to a particular temperature and the activity of this fraction after the incubation period is then compared at the particular temperature with the activity of the fraction which was not incubated at the particular temperature. The corresponding value is typically recorded in %.

"pH stability" refers to the characteristic of an enzyme which may be determined by dividing an enzyme preparation into two fractions one of which is exposed to a particular pH value and the activity of this fraction after the incubation period at the particular pH value is then compared with the activity of the fraction which was not incubated at the particular pH value. The corresponding value is typically recorded in %.

SHORT DESCRIPTION OF THE INVENTION

The present invention relates to polypeptides with β-pyranosidase activity comprising an amino acid sequence having at least 71%, if possible at least 75%, if possible at least 80%, and preferably at least 85% sequence identity with SEQ ID NO 2. SEQ ID NO. 2 is contained in SEQ ID NO. 1. SEQ ID NO. 1 contains a polypeptide which is called FgXyl3a in the following. The underlying DNA is represented by SEQ ID NO. 3. It was isolated from the gene bank clone Bgl13 which contains a section of genomic DNA from *Fervidobacterium gondwanense* (*F. gondwanense*).

The invention also relates to polypeptides comprising an amino acid sequence which have at least 70%, if possible at least 75%, if possible at least 80%, and preferably at least 85% sequence identity with SEQ ID NO. 1. The invention further comprises polypeptides comprising a structural domain 1 of a glycoside hydrolase of family 3 (GHF3) and a structural domain 2 of a glycosidehydrolase of family 3 (GHF3) wherein at least one of these two domains has at least 70%, if possible at least 75%, if possible at least 80%, and preferably at least 85% sequence identity with the corresponding domain FgXyl3a. Structural domain 1 of FgXyl3a consists of the region comprising the amino acid residues 13 to 381 and 586 to 383 of SEQ ID NO. 1; structural domain 2 of FgXyl3a consists of the region comprising the amino acid residues 382 to 585 of SEQ ID NO. 1.

The β-pyranosidase activity of the polypeptide according to the present invention is selected from β-xylopyranosidase activity, β-glucopyranosidase activity and of a combination of these two activities, the β-xylopyranosidase activity being preferred.

In a preferred embodiment, the present invention relates to a polypeptide with β-pyranosidase activity, the amino acid sequence of which corresponds to at least one of the above criteria and which is capable of decomposing at least one β-glycosidic bond contained in the following substrates: xylobiose, xylotriose, xylotetraose, xylan.

In a more preferred embodiment, the present invention relates to a polypeptide with β-pyranosidase activity which satisfies at least one of the above criteria and the activity of which vis-à-vis pNP-β-cellobioside is markedly lower than vis-à-vis pNP-β-xylobioside, namely 5% or less vis-à-vis pNP-β-cellobioside as compared with the activity vis-à-vis pNP-β-xylobioside (pNP representing para-nitrophenyl in this specification).

In a yet more preferred embodiment, the present invention relates to a polypeptide with β-pyranosidase activity which corresponds to at least one of the above criteria and which has maximum activity vis-à-vis pNP-β-xylopyranoside in the acidic, neutral or slightly alkaline range, i.e. in a range from pH 4.0 to pH 8.0, therein, if possible, in the slightly acidic to neutral range, i.e. in a range from pH 5.5 to 7.0, and preferably in a range of pH 6.2 to 6.8.

In a yet more preferred embodiment, the present invention relates to a pH-stable polypeptide with β-pyranosidase activity which corresponds to at least one of the above criteria and the maximum activity of which vis-à-vis pNP-β-xylopyranoside is at least 50%, if possible at least 60%, if possible at least 70%, and preferably at least 80% after 48 hours of incubation at pH 9.0.

In a yet more preferred embodiment, the present invention relates to a polypeptide with β-pyranosidase activity, which polypeptide is active at high temperature, and which satisfies at least one of the above criteria, and which has maximum activity vis-à-vis pNP β-xylopyranoside in a range between 60° C. and 100° C., if possible between 70° C. and 95° C., and preferably between 80° C. and 90° C.

In a yet more preferred embodiment, the present invention relates to a temperature-stable polypeptide with β-pyranosidase activity which satisfies at least one of the above criteria and the maximum activity of which vis-à-vis pNP-β-xylopyranose after three hours of incubation at 60° C. is at least 40%, preferably at least 50%.

In a more preferred embodiment, the polypeptide which satisfies at least one of the above criteria may be present as a fusion protein; it is preferably fused to one of the following: a carbohydrate binding domain of another protein, a signal peptide, an affinity tag or a protease cleavage site.

The present invention also relates to a mixture containing the polypeptide with β-pyranosidase activity which satisfies at least one of the above criteria and one or more pectinases and/or one or more endoxylanases and/or one or more β-glucosidases and/or one or more β-glucanases and/or one or more cellobiohydrolases and/or one or more β-xylosidases and/or one or more α-arabinofuranosidases and/or one or more α-glucuronidases and/or one or more acetyl xylan esterases.

The present invention also relates to a nucleic acid which encodes the polypeptide described above, and to a vector containing said nucleic acid.

The present invention also relates to a host cell transformed with the vector described above. The host cell according to the present invention may be a prokaryote or a eukaryote. A eukaryotic host cell is preferably selected from the group consisting of Saccharomyces cerevisiae, Yarrowia lipolytica, Schizosaccharomyces lactis, Kluyveromyces lactis, Pichia methanolytica, Pichia pastoris, Pichia angusta, Hansenula polymorpha, Aspergillus niger, Chrysosporium lucknowense, Trichoderma reesei, Penicillum sp.

In a particularly preferred embodiment, the eukaryotic host cell is a methylotrophic yeast, preferably from the group comprising Pichia methanolytica, Pichia pastoria, Pichia angusta, Hansenula polymorpha.

A prokaryotic host cell according to the present invention is preferably selected from the group comprising Bacillus sp., Bacillus subtilis, Bacillus licheniformis, Bacillus megaterium, Thermus thermophilus, Pseudomonas fluorescens, Fervidobacterium sp., Escherichia coli.

The present invention also relates to a method for purifying the above polypeptide with β-pyranosidase activity comprising the following steps:

a) obtaining the host cell transformed with the vector described above;
b) cultivating the host cell under conditions where the polypeptide with β-pyranosidase activity is expressed,
c) purifying the polypeptide with β-pyranosidase activity.

In a preferred embodiment, step c) of the method for purifying the polypeptide with β-pyranosidase activity described above comprises heat precipitation.

The present invention also relates to the use of the polypeptide with β-pyranosidase activity described above or of the mixture described above containing the polypeptide with β-pyranosidase activity described above for degrading one or more of the following substrates: β-xylopyranoside or β-glucopyranoside.

In a preferred embodiment, the present invention relates to the use described above for the enzymatic degradation of biomass containing lignocellulose and/or for textile processing and/or as an additive to detergents and/or in the food and/or feed industry.

In a preferred embodiment, the present invention relates to the use described above for preparing fruit juices and/or for preparing wine or beverages containing wine, and/or for the preparation of beer or beverages containing beer, and/or for the preparation of oil, preferably olive oil, rapeseed oil or sunflower oil and/or for the preparation of baked goods.

DETAILED DESCRIPTION OF THE INVENTION

Polypeptides with β-Pyranosidase Activity

The present invention relates to polypeptides with β-pyranosidase activity comprising an amino acid sequence having at least 71%, if possible at least 75%, if possible at least 80%, and preferably at least 85% sequence identity with SEQ ID NO 2. The sequence identity is determined as described in the section "Definitions".

SEQ ID NO. 2 is contained in SEQ ID NO. 1. SEQ ID NO. 1 contains the amino acid sequence of the polypeptide FgXyl3a. The DNA underlying the SEQ ID NO. 1, represented by SEQ ID NO. 3, originates from the gene bank clone Bgl13 which contains a section of genomic DNA from Fervidobacterium gondwanense (F. gondwanense). Finding the SEQ ID NO. 3 and determining the domain structure are described in detail in example 3.

In short, SEQ ID NO. 2 comprises that region of SEQ ID NO. 1 which contains both structural domains of the glycoside hydrolase and was determined by a sequence comparison with SEQ ID NO. 4 (enzyme BglB of Thermotoga neapolitana, Pozzo et al., 2010, J. Mol. Biol., 2: 397 (3), 724-739). SEQ ID NO. 2 thus comprises amino acid residues 13 to 638 of SEQ ID NO. 1.

The present invention also relates to polypeptides comprising an amino acid sequence which has at least 70%, if possible at least 75%, if possible at least 80%, and preferably at least 85% sequence identity with SEQ ID NO. 1.

The invention further comprises polypeptides comprising a structural domain 1 of a glycoside hydrolase of family 3 (GHF3) and a structural domain 2 of a glycoside hydrolase of family 3 (GHF3), wherein at least one of these two domains has at least 70%, if possible at least 75%, if possible at least 80%, and preferably at least 85% sequence identity with the corresponding domain FgXyl3a, hat. Structural domain 1 of FgXyl3a consists of the region comprising amino acid residues 13 to 381 and 586 to 383 of SEQ ID NO. 1; the structural domain 2 of FgXyl3a consists of the region comprising the amino acid residues 382 to 585 of SEQ ID NO. 1. The method for determining structural domains is described in example 1. It may be applied generally to polypeptides the sequence identity of which satisfies at least the criteria described herein.

The cloning (example 2), expression (example 3), purification from a cell extract (examples 4 and 5) and determination of the molecular weight (example 6) of a polypeptide with β-pyranosidase activity according to the present invention are described in the examples.

The β-pyranosidase activity of the polypeptide according to the present invention is selected from β-xylopyranosidase activity, β-glucopyranosidase activity and a combination of these two activities, the β-xylopyranosidase activity being preferred. The detection of activity and the determination of the substrate specificity of a polypeptide according to the present invention are described in detail in examples 7 and 8.

In a preferred embodiment, the present invention relates to a polypeptide with β-pyranosidase activity which satisfies at least one of the above criteria and which is capable of hydrolysing at least one of the β-glycoside bonds contained in the following substrates: xylobiose, xylotriose, xylotetraose, xylan. The determination of the hydrolysis products of a polypeptide with β-pyranosidase activity is described in detail in example 13.

In more preferred embodiment, the present invention relates to a polypeptide with β-pyranosidase activity which satisfies at least one of the above criteria and the activity of which vis-àvis pNP-β-cellobioside is markedly lower than vis-àvis pNP-β-xylobioside, namely 5% or less vis-àvis pNP-β-cellobioside compared with the activity vis-àvis pNP-β-xylobioside. A method for determining substrate specificity is described in example 8.

In a yet more preferred embodiment, the present invention relates to a polypeptide with β-pyranosidase activity which satisfies at least one of the above criteria and which has maximum activity vis-àvis pNP-β-xylopyranoside in the acidic, neutral or slightly basic range, i.e. in a range of pH 4.0 to pH 8.0, therein, if possible, in the slightly acidic to neutral range, i.e. in a range of pH 5.5 to 7.0, and preferably in a range of pH 6.2 to 6.8. A method for determining the influence of the pH value on the activity of a polypeptide with β-pyranosidase activity is described in more detail in example 11.

In a yet more preferred embodiment, the present invention relates to a pH-stable polypeptide with β-pyranosidase activity which satisfies at least one of the above criteria and the maximum activity of which vis-àvis pNP-β-xylopyranoside after 48 hours of incubation at a pH of 9.0 is at least 50%, if possible at least 60%, if possible at least 70%, and preferably at least 80%. A method for determining the influence of the pH value on the activity of a polypeptide with β-pyranosidase activity is described in more detail in example 11.

In a yet more preferred embodiment, the present invention relates to a polypeptide with β-pyranosidase activity which is active at high temperature and which satisfies at least one of the above criteria and which has maximum activity vis-àvis pNP-β-xylopyranoside in a range between 60° C. and 100° C., if possible between 70° C. and 95° C., and preferably between 80° C. and 90° C. A method for determining the influence of the temperature on the activity of a polypeptide with β-pyranosidase activity is described in more detail in example 9.

In an yet more preferred embodiment, the present invention relates to a temperature-stable polypeptide with β-pyranosidase activity which satisfies at least one of the above criteria and the maximum activity of which vis-àvis pNP-β-xylopyranoside after 3 hours of incubation at 60° C. is at least 40%, preferably at least 50%. A method for determining the influence of the temperature stability on the activity of a polypeptide with β-pyranosidase activity is described in more detail in example 10.

Fusion Protein

The polypeptide according to the present invention may either occur in the isolated form or it may be fused to one or more additional oligo- or polypeptides. That is, in a further preferred embodiment the polypeptide satisfying at least one of the criteria described above may be present as a fusion protein, wherein it is preferably fused to one of the following: a carbohydrate binding domain of another protein, a signal peptide, an affinity tag or a protease cleavage site.

The fusion protein according to the present invention is not limited to the method by which it has been obtained but comprises fusion proteins of all kinds as long as they contain a component satisfying at least one of the above criteria. One option is to obtain the fusion protein according to the present invention by methods of molecular biology. As a person skilled in the art will know, methods for preparing nucleic acids encoding fusion proteins are standard methods of molecular biology which are described in greater detail, for example, in Sambrook et al. (Molecular cloning, a laboratory manual, 2$^{nd}$ edition, 1989, Cold Spring Harbor Laboratory Press, Cold Spring Harbor, N.Y.). In a preferred embodiment, the fusion protein besides the polypeptide with β-xylosidase activity according to the present invention may be fused to a carbohydrate binding domain of another protein. In a preferred embodiment, the polypeptide with β-xylosidase activity according to the present invention may be fused to a polypeptide selected from one or more of the following group: signal peptide, affinity tags, protease cleavage site. Translational coupling may be used to direct the expressed polypeptide according to the present invention to cellular compartments or organelles or to export it from the host cell. Signal peptides which are also called signal sequences are well known to a person skilled in the art and include the lead sequences of the periplasmatic proteins OmpA, OmpT, PelB, PhoA. Signal sequences for the export of proteins are found, for example, in naturally occurring secreted proteins, for example proteins with carbohydrate-modifying characteristics such as cellobiohydrolase I or II, endoglucanasae, AmyE, and in *S. cerevisiae* Mfα or chicken egg lysozyme. Cleavage sites for proteases which are suitable as tags for recombinantly expressed proteins are well known to a person skilled in the art. Protease cleavage site means a poly- or oligopeptide comprising a peptide bond which may be specifically cleaved by a certain protease, and a recognition sequence which is usually near the cleavage site and is recognised by the corresponding protease. The protease cleavage sites that may be used in accordance with the present invention are not subject to any limitation. They expressly include the cleavage site of the tobacco etch virus (TEV) protease, the cleavage sites of the blood coagulation factors from mammals such as factor Xa or thrombin. The affinity tags that may be used according to the present invention are not subject to any limitations. As a person skilled in the art knows, affinity tags that have proved to be advantageous for the purification of many polypeptides are described in detail, for example, in Sambrook et al. (Molecular cloning, a laboratory manual, 2nd edition, 1989, Cold Spring Harbor Laboratory Press, Cold Spring Harbor, N.Y.). Expressly included in the definition of the present invention is an oligohistidine tag as described in examples 1 and 5.

Enzyme Mixture

A mixture of enzymes may also be used in accordance with the invention. This mixture contains the polypeptide with β-pyranosidase activity which satisfies at least one of the above criteria and comprises one, two or more additional enzymes. These additional enzymes may be selected from the group comprising pectinases, endoxylanases, β-glucosidases, β-glucanases, cellobiohydrolases, β-xylosidases, α-arabinofuranosidases, α-glucuronidases, acetyl xylan esterases. The enzyme mixture according to the invention thus comprises the polypeptide with β-pyranosidase activity which satisfies at least one of the criteria described above and one or more pectinases and/or one or more endoxylanases and/or one or more β-glucosidases and/or one or more β-glucanases and/or one or more cellobiohydrolases and/or one or more β-xylosidases and/or one or more α-arabinofuranosidases and/or one or more α-glucuronidases and/or one or more acetyl xylan esterases.

In a preferred embodiment, the enzyme mixture according to the invention comprises the polypeptide with β-pyranosidase activity which satisfies at least one of the criteria described above and one or more of α-arabinofuranosidases and/or one or more α-glucuronidases and/or one or more acetyl xylan esterases.

Unless specifically stated otherwise, the term "comprises" in the present application is used to indicate that further components may optionally be present in addition to the components listed under "comprises". However, it is considered a special embodiment that the term "comprises" includes the possibility that no other components are present, i.e. the term "comprises" under this special embodiment is understood to mean the same as "consists of".

Nucleic Acid and Vector

The present invention also relates to a nucleic acid encoding the polypeptides described above. One example for such a nucleic acid is shown by SEQ ID NO. 3. The nucleic acid according to the present invention may be a component of an expression cassette. A person skilled in the art will be well aware of the typical components of an expression cassette; for example, they are described in more detail in Sambrook et al. (Molecular cloning, a laboratory manual, $2^{nd}$ edition, 1989, Cold Spring Harbor Laboratory Press, Cold Spring Harbor, N.Y.). In addition to the coding sequence, the expression cassette typically contains at least: one promoter and one terminator. The expression level of a gene encoding a polypeptide according to the present invention may be adjusted by the number of copies of the gene introduced into the host cell; preferably more than one copy is present. The promoter may be adjusted for optimised expression so that it will, for example, respond to the addition of a chemical or the change of one or more physical parameters in such a manner that the induction of a gene may be switched on or off. Examples for inducible promoters include the tetracycline repressor system, the Lac-repressor system (Beneyx, 1999, Curr. Opin. Biotechnol. 10: 411: 422), systems inducible by copper ions (Hottinger et al., 2004, Yeast, 10: 283-296), systems inducible by methanol (Cereghino et al., 2000, FEMS Microbiol. Reviews 24: 45-66) or the temperature-inducible λPL promoter. Alternatively, derepression of the promoter by reaching a favourable physiological state of the culture may be a useful strategy (promoters PhoA, Trp, Adh2, Fmdh, CBH1 (Price et al., 1990, Methods Enzymol., 185-308-318; Hollenberg, 1995, U.S. Pat. No. 3,589,585). Methods to further increase the yield include the co-expression of one or more proteins involved in the translation, proteins involved in target control, proteins involved in folding (for example chaperones of the Hsp70-family, protein disulfide isomerases), or of proteases assisting correct processing.

The expression cassette may be integrated in a vector which is either propagated episomally in the host cell or is integrated in its genome. Examples of typical vectors are bacterial plasmids, yeast plasmids, centromer-containing linear DNA, constructs of viral origin such as SV40, phage DNA, bacculovirus, vaccinia, adenovirus, chicken pox virus, pseudo-rabies and combinations of vectors of bacterial, eukaryotic and viral origin. Integration may be achieved by methods well known to a person skilled in the art of molecular biology, such as homologous recombination, transposition, or by using viral transfection systems. Also included are episomal systems for expression, one or more copies of which are integrated into the genome of the host cell either in a planned or unplanned manner. Moreover all vector systems are included which permit the heterologous expression of a polypeptide according to the invention in a host cell.

Host Cell

The present invention also relates to a host cell transformed with the vector described above. Preferred methods for introducing the vector construct into the host cell include transformation, transfection, conjugation and hybridisation. Transformation may be effected by electroporation, protoplast fusion, lipofection, ballistic bombardment, chemical transformation based on calcium chloride, polyethylene glycol (PEG) or manganese chloride. Other strategies include the application of viral particles. Another option is the use of naturally competent organisms as host cells.

The host cell according to the present invention may be a prokaryote or a eukaryote. A eukaryotic host cell is preferably selected from the groups consisting of *Saccharomyces cerevisiae, Yarrowia lipolytica, Schizosaccharomyces lactis, Kluyveromyces lactis, Pichia methanolytica, Pichia pastoris, Pichia angusta, Hansenula polymorpha, Aspergillus niger, Chrysosporium lucknowense, Trichoderma reesei, Penicillum* sp.

In a particularly preferred embodiment, the eukaryotic host cell is a methylotrophic yeast, preferably from the group including *Pichia methanolytica, Pichia pastoria, Pichia angusta, Hansenula polymorpha*.

A prokaryotic host cell according to the present invention is preferably selected from the group comprising *Bacillus* sp., *Bacillus subtilis, Bacillus licheniformis, Bacillus megaterium, Thermus thermophilus, Pseudomonas fluorescens, Fervidobacterium* sp., *Escherichia coli*.

After transformation of the host cell and growth to the desired cell density, the selected inducible promoter may be induced by a chemical activator or by changing one or more physical parameters so as to induce the cultivated host cells to produce the desired polypeptide.

Purification Method

The present invention also relates to a method for purifying the above-described polypeptide with β-pyranosidase activity. In a particular embodiment, the polypeptide is not secreted by the host cell. After culturing, the host cells are then isolated and the polypeptide according to the present invention contained therein is isolated. Such a process is described in examples 3 to 5. In a particular embodiment, the polypeptide according to the present invention is produced as a fusion protein with at least one signal peptide which directs the recombinant protein to secretion from the host cell.

In detail, the process comprises the following steps:
  a) obtaining the host cell transformed with a vector as described above;

b) cultivating the host cell under conditions where the polypeptide with β-pyranosidase activity is expressed, c) purifying the polypeptide with β-pyranosidase activity.

The host cell according to a) may be recovered by methods well known to a person skilled in the art, for example as described in the chapter "host cell".

The manner in which step b) is performed is influenced by many factors which are basically known to a person skilled in the art. Thus the growth medium, the growth temperature and other conditions of growth are selected depending on the kind of host cell used. The conditions under which the polypeptide is expressed further depend especially on the selection of the promoter used as described above. Different methods for harvesting host cells from a protein-expressing cell culture are well known to a person skilled in the art and include, for example, centrifugation of the medium containing the host cells and filtration of the medium containing the host cells. Then the cells are typically subjected to lysis, either by chemical or mechanical methods or by a combination of both.

The manner of performing step c) is selected depending on the nature of the expressed polypeptide. In particular embodiments, in which a fusion protein containing the polypeptide according to the present invention and another domain such as an affinity tag is expressed, the characteristics of the affinity tag may also be used to purify the fusion protein. One example for such an affinity tag is a tag comprising several, typically at least six, histidine residues as described in examples 3 to 5.

In a preferred embodiment, step c) of the process for purifying the polypeptide described above comprises heat precipitation. For this purpose, a mixture of different polypeptides comprising the desired polypeptide is brought to a certain temperature which is generally higher than the temperature at which the host cell grew during expression. This mixture may comprise two or more different polypeptides. Such a mixture may also be a lysate which is produced when the cells expressing the desired polypeptides are subjected to lysis, for example with mechanical or chemical methods or a combination of both, or an extract obtained or enriched from said lysate.

Depending on their properties, different proteins precipitate at different elevated temperatures. In this way, an enrichment in the in the cell lysate or the extract recovered therefrom can be achieved. By further increasing the temperature, the desired protein may optionally be precipitated.

Use

The present invention also relates to the use of the polypeptide with β-pyranosidase activity or the mixture containing the polypeptide with β-pyranosidase activity described above for any purpose for which such enzyme activity is required or desired.

In particular, the present invention describes the use of the polypeptide with β-pyranosidase activity or the mixture containing the polypeptide with β-pyranosidase activity for degrading one or more substrates containing one or more β-xylopyranosidic and/or one or more β-glucopyranosidic bonds, hereinafter called β-xylopyranoside or β-glucopyranoside.

In a preferred embodiment, the present invention relates to the above-described use for the enzymatic degradation of biomass containing lignocellulose.

In a more preferred embodiment, the present invention relates to the above-described use in textile processing. In a particularly preferred embodiment, the present invention relates to the above-described use as an additive to detergents. In a further particularly preferred embodiment, the present invention relates to the above-described use in the food and/or feed industry. Finally, in a further particularly preferred embodiment, the present invention relates to a combination of two or more of these applications.

In a particularly preferred embodiment, the present invention relates to the above-described use for the production of fruit juices. In a more preferred embodiment, the present invention relates to the above-described use for the production of wine or beverages containing wine, and in a further more preferred embodiment, the present invention relates to the above-described use for the production of beer or beverages containing beer. In a further more preferred embodiment, the present invention relates to the above-described use for the production of oil, preferably olive oil, rapeseed oil or sunflower oil. Finally, in a further more preferred embodiment, the present invention relates to the above-described use for the production of baked goods.

EXAMPLES

Example 1

Identification and Characterisation of β-Pyranosidase FgXyl3A of *Fervidobacterium Gondwanense*

For identification of cellulolytic and xylanolytic activity, a gene bank of *F. gondwanense* was screened. The gene bank was prepared according to the following method: Genomic DNA was purified from *Fervidobacterium gondwanense* cells using the Qiagen genomic DNA isolation kit (Qiagen GmbH, Hilden). The DNA obtained was degraded into clonable fragments of several kilo bases in length by partial digestion with Sau3A1; these fragments were ligated with lambda-ZAP-Express-Predigested (Stratagene™) vector arms and the ligation products then packed into phage particles as instructed by the manufacturer. The primary phage library was amplified in *E. coli* XL1-Blue MRF' cells and the phagemide library cut out by means of helper phages ExAssist and stably established after transfection in *E. coli* XLOLR.

For sample taking, bacteria of the *E. coli* strain XLOLR containing parts of the genome of *F. gondwanense* in the vector pBK-CMV (kanamycin resistance, phagemide vector with Lac-Promoter, Agilent Technologies, Waldbronn) were plated on an LB selection tray and incubated at 37° C. over night. The colonies that had grown were transferred to a fresh medium and reincubated at 37° C. over night.

For the identification of colonies with β-glucosidase activity, esculin (Sigma-Aldrich, Munich) was used as a substrate. For this purpose, the colonies were detected coated with esculin agar (0.1% (w/v) esculin, 0.01% (w/v) ammonium iron(III) citrate, 50 mM Na-acetate, 1% (w/v) agarose, pH 6.0). It was possible to detect activity from the formation of a brown halo around the colonies which is due to the decomposition of the esculin into glucose and esculetin. Esculetin forms a complex with iron ions which becomes visible by the brown colouring. Clones with enzymatic activity were isolated and cultivated.

Screening with the substrate esculin by means of colorimetric detection methods resulted in the identification of the gene bank clones Bgl13.

In order to determine the open reading frames (ORFs) encoding the active protein, the plasmid of clone Bgl13 was sequenced by means of primer walking using the standard primers T3 and T7.

```
T3      5'-ATTAACCCTCACTAAAGGGA-3'

T7      5'-TAATACGACTCACTATAGGG-3'
```

This standard method is described in more detail in Sambrook et al. (Molecular cloning, a laboratory manual, 2$^{nd}$ edition, 1989, Cold Spring Harbor Laboratory Press, Cold Spring Harbor, N.Y.).

The overall size of the inserts was 8479 base pairs (bp). For identification of open reading frames on the insert, the "ORF Finder" from the NCBI data base was used; five open reading frames were determined. So as to be able to allocate a possible function to the proteins encoded by the ORFs, their amino acid sequences were compared with known sequences by means of "blastp" from the NCBI-data base. BLAST represents the "Basic Local Alignment Search Tool" (Altschul et al., 1997, Nucleic Acids Res 25 (17): 3389-3402). The amino acid sequence of ORF 1 displayed similarities with β-xylosidases of the glycoside hydrolase family 3 and, according to the respective nomenclature for glycoside hydrolases, ORF 1 was designated xyl3A and the corresponding protein FgXyl3A (Henrissat et al., 1998, FEBS Lett. 425 (2): 352-354).

The gene xyl3A encoding the β-pyranosidase consists of 2328 bp and encodes the protein FgXyl3A with of a size of 775 amino acids. FgXyl3A has a calculated molecular weight of 85.9 kilodalton (kDa) and a theoretical isoelectric point (pI) of 5.55. A signal sequence could not be determined by "SignalP 3.0".

The amino acid sequence of FgXyl3A is shown in SEQ ID NO. 1.

A sequence comparison of FgXyl3A with sequences of known β-xylosidases was performed with the aid of "blastp" from the NCBI data base. The amino acid sequence of FgXyl3A showed the highest congruence with a putative β-xylosidase of the glycoside hydrolase family 3 of *Thermotoga neapolitana* with an identity of 68%. The sequence of FgXyl3A contains the preserved amino acids which are characteristic for proteins of the glycoside hydrolase family 3 (Zverlov et al., 1997, Microbiology 143 (Pt 11): 3537-3542).

The domain structure of FgXyl3A was determined with the aid of "InterProScan". Accordingly, the protein FgXyl3A consists of two domains, namely of an N-terminal catalytic domain and of a C-terminal domain, both domains showing similarity to the glycoside hydrolase family 3 (FIG. 1).

SEQ ID NO. 1 contains a region which comprises the two structural domains determined by a sequence comparison with the protein BgIB of *Thermotoga neapolitana* (Pozzo et al., 2010, J. Mol. Biol., 2:397 (3), 724-739). Structural domain 1 contains the amino acid residues Leu13 to Ile381 and Gln586 to Tyr638 of SEQ ID NO. 1 and was determined by a sequence comparison by means of InterProScan with SEQ ID NO. 4. A conserved aspartate residue is present there (Asp281) which was identified as a catalytic nucleophil in glycoside hydrolases of the family 3 (Zverlov et al., 1997, Microbiology 143 (Pt 11): 3537-3542; Wulff-Strobel & Wilson, 1995, J. Bacteriol. 177 (20): 5884-5890).

Structural domain 2 contains the amino acid residues Val382 to Val585 of SEQ ID NO. 1 and was determined by a sequence comparison by means of InterProScan with SEQ SD NO. 4. SEQ ID NO. 2 is the region of SEQ ID NO. 1 which includes both structural domains and hence comprises the amino acid residues 13 to 638 of SEQ ID NO. 1.

The underlying nucleotide sequence of the full-length protein FgXyl3a is given by SEQ ID NO. 3.

Example 2

Cloning the β-Pyranosidase FgXyl3A of *Fervidobacterium Gondwanense*

For cloning xyl3A, the gene was amplified by means of the following oligonucleotides by a polymerase chain reaction (PCR) according to Sambrook et al. (Molecular cloning, a laboratory manual, 2$^{nd}$ edition, 1989. Cold Spring Harbor Laboratory Press, Cold Spring Harbor, N.Y.):

```
xyl3A_BamHIF    5'-GGGGATCCGAGATATATAAGGATTCTTC-3' xyl3A_HindIII.R  5'-GGAAGCTTTTAGAAAGTGTAAACTTTTG-3'
```

The oligonucleotides contained a BamHI cleavage site at the 5' terminus and a HindIII cleavage site at the 3' terminus. The PCR was performed in a thermal cycler (Gene Amp PGR System 2400, Perkin-Elmer, Massachusetts, USA) and the PCR products purified with the "High Pure PCR Product Purification Kit" (Roche Diagnostics, Mannheim) as instructed by the manufacturer. The amplified gene was ligated into the vector pJET1.2 ("CloneJET™ PCR Cloning Kit" (Fermentas, St. Leon-Rot)) with the aid of the 3'A overhangs formed by high fidelity polymerase in accordance with the instructions of the manufacturer. By restriction with the endonucleases BamHI and HindIII, the gene xyl3A was cut from the vector and ligated into the vector pQE-30 cut with the same restriction enzymes (ampicillin resistance, expression vector with a sequence for an N-terminal 6× histidine tag with T5-Promotor, Qiagen, Hilden). Correct cloning of xyl3A into the vector pQE-30 was verified by sequencing. For gene expression, the recombinant plasmid pQE-30::xyl3A (FIG. 2) was transformed into the *E. coli* strain M15[pREP4] (Nal$^s$ Str$^s$ Rif$^s$ Thi$^-$ Lac$^-$ Ara$^+$ Gal$^+$ Mtl$^-$ F$^-$ RecA$^+$, Uvr$^+$ Lon$^+$ pREP4, Qiagen Hilden). By cloning xyl3A into the pQE-30 vector a sequence encoding a His tag was attached to the 5' terminus of the gene. This results in a size of 786 amino acids and a calculated molecular weight of 87.2 kDa for the recombinant protein FgXyl3A.

Example 3

Expression of Fgxyl3A in *Escherichia coli* (*E. coli*)

The recombinant clone of *Escherichia coli* (*E. coli*) M15/pQ E-30::xyl3A (example 2) was incubated at 37° C. Cell cultivation of the *E. coli* strains was performed in LB-Medium (10 g/l of trypton, 5 g/l of yeast extract, 10 g/of 1 NaCl, pH 7.0) according to Sambrook et al. (Molecular cloning, a laboratory manual, 2$^{nd}$ edition, 1989, Cold Spring Harbor Laboratory Press, Cold Spring Harbor, N.Y.).

The cultivation of strains with plasmid- or genome-coded resistance against antibiotics was performed under selection pressure by adding the appropriate antibiotic. The concentration of antibiotics used corresponded to the recommendations of Sambrook et al. (Molecular cloning, a laboratory manual, 2$^{nd}$ edition, 1989, Cold Spring Harbor Laboratory Press, Cold Spring Harbor, N.Y.). The cultivation of the cells was carried out aerobically at 37° C. on a shaker (Certomat R, B. Braun Biotech International, Melsungen) at 160 rpm. The growth of the cells was determined on the basis of the optical density (OD) at a wavelength of 600 nm in a spectrophotometer (UV-1602, Shimadzu Deutschland, Duisburg). The induction of the gene expression of recombinant *E. coli* strains was performed by adding 1 mM of isopropyl-β-D-thiogalactopyranoside (IPTG) at an $OD_{600}$ nm of 0.6-0.8. This was followed by the incubation of the cells at 37° C. and 160 rpm for 4.5 hrs and subsequent centrifugation of the cells in a Sorvall RC 5C Plus centrifuge (Thermo Fisher Scientific, Langenselbold) for 20 minutes at 4221×g and 4° C., obtaining about 2.0 g of cells (humid weight) of 500 ml culture volume. The pellet was used directly for the preparation of cell-free crude extract (example 4) or stored at –20° C.

Example 4

Preparation of a Crude Extract of the Recombinant *E. coli* Clone M15/pQE-30::xyl3A For obtaining a crude extract, the cell pellet (example 3) was washed twice in lysis buffer (50 mM of $NaH_2PO_4$, 300 mM of NaCl, 10 mM of imidazole, pH 8.0), with 20 minutes of centrifugation at 4500×g and 4° C. each time. The pellet was then taken up in a cell lysis buffer, using 5 ml of lysis buffer per 1 g of cells. This was followed by cell lysis by means of ultrasound (Branson Sonifier®, Danbury, Conn., USA), wherein 3 cycles were performed for 5 minutes each on ice (output control: 50%, duty cycle: 5). Cell debris was then separated by centrifugation for 20 minutes at 20200×g and 4° C. and the supernatant transferred into a new vessel. Optionally, heat precipitation of the crude extract was performed at 60° C. for 15 minutes and the precipitated protein separated by centrifugation for 20 minutes at 20200×g and 4° C. The crude extract was stored at 4° C.

The crude extract was tested for β-xylosidase activity by a standard test (example 7) and used for purification (example 5).

Example 5

Purification of FgXyl3A

The multi-step purification of FgXyl3A by (1) heat precipitation, (2) affinity chromatography and (3) gel filtration resulted in the almost complete purification of the protein.

(1) Heat precipitation: After the first purification step by means of heat precipitation (example 4), a yield of 41.7% was obtained (Table 1).

(2) Affinity chromatography: The further purification of FgXyl3A with an attached His tag (examples 2, 3 and 4) was achieved through affinity chromatography by means of $Ni^{2+}$ nitrilotriacetic acid ($Ni^{2+}$-NTA, Qiagen, Hilden). An AKTA™ purifier system (GE Healthcare, Munich) with the following components was used for performing the affinity chromatography: monitor UV-900, pump P-900, in-line mixer M-925, motor valve INV-907 and fraction collector Frac-950. The buffers used were filtered before use (0.45 μm cellulose mixed ester filter, Whatman, Dassel) and the protein samples centrifuged for 10 minutes at 13000×g and 4° C. After equilibration of the column matrix with 5 ml column volumes of cell lysis buffer, the crude extract or heat-precipitated crude extract was loaded onto the column at a flow rate of 1 ml/minute. Unbound proteins were removed by washing of the column matrix with 3 column volumes of washing buffer (50 mM of $NaH_2PO_4$, 300 mM of NaCl, 20 mM imidazole, pH 8.0) at a flow rate of 2 ml/minutes. The elution of bound proteins was performed by rinsing the column with 5 column volumes of elution buffer (50 mM $NaH_2PO_4$, 300 mM of NaCl, 250 mM imidazole, pH 8.0) at a flow rate of 2 ml/minute. The fraction size of the samples collected was 2 ml. The fractions containing the target protein were combined, concentrated with the aid of micro-concentrators (Amicon Ultra-15 centrifugal filter unit, 10 kDa cut-off size, Milipore, Schwalbach) and used for further purifications steps or, respectively, subjected to dialysis and used for biochemical characterisation.

This further purification by means of $Ni^{2+}$-NTA agarose resulted in a marked loss in yield which was 1.13%.

(3) Gel filtration: For the further purification of FgXyl3A with an attached His tag (examples 2, 3 and 4) by means of gel filtration, an AKTA™ Fast Protein Liquid Chromatography (FPLC) plant (GE Healthcare, Munich) with the following components was used: monitor UPC-900, pump P-920, in-line mixer M-925, engine valve INV-907 and fraction collector Frac-950. The purification by means of gel filtration was performed by a HiLoad 16/60 Superdex 200 prep grade column (GE Healthcare, Munich). The protein samples were centrifuged for 10 minutes at 13000×g and 4° C. before use and the used buffers filtered (0.45 μm cellulose mixed ester filter, Whatman, Dassel). At a flow rate of 1 ml/minute the column was loaded with 1 ml of the protein sample maximum and rinsed with 1.5 column volumes of 50 mM $Na_2HPO_4$ and 150 mM of NaCl (pH 7.0). Fractions of a size of 2 ml were collected. The fractions containing the target protein were combined and concentrated with the aid of micro-concentrators (Amicon Ultra-15 centrifugal filter unit, 10 kDa cut-off size, Milipore, Schwalbach). Subsequent desalting and the change of buffers of protein solutions was achieved by dialysis. For this purpose, dialysis tubing (MembraCel MWCO 3500, Serva, Heidelberg) was boiled in the buffer used and then loaded with the protein sample. Dialysis was performed in 50 mM Na-acetate, pH 6.0 and, respectively, pH 6.5 over night at 4° C. with stirring against the 100-fold volume of the protein solution. After dialysis, the samples were used for biochemical characterisation. As a result of the last purification step by gel filtration a yield of 0.18% and a purification factor of 95 was obtained. The specific activity was 20.9 U/mg vis-à-vis pNP-β-xylopyranoside (Table 1).

Figure 3:
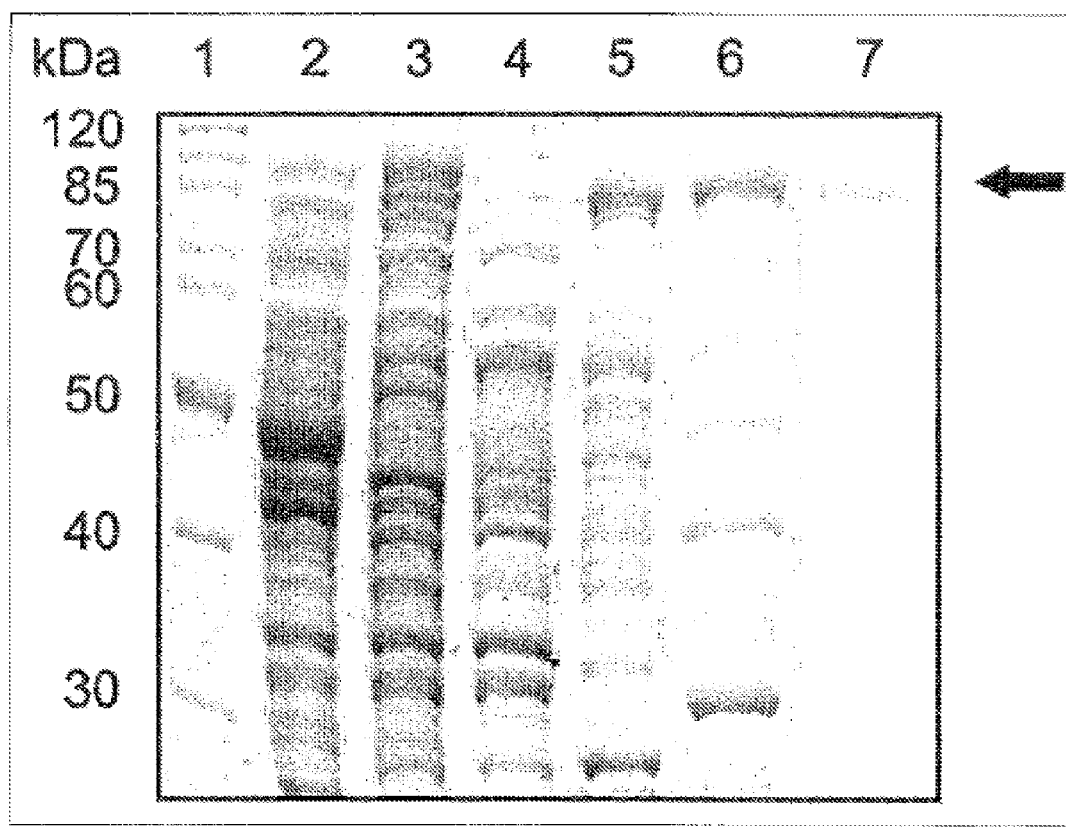

The purification of histidine-tagged FgXyl3a is shown in FIG. 3 and Table 1.

| Purification step | Total protein [mg] | Overall activity [U] | Specific activity [U/mg] | Yield (%) | Purification factor [x-fold] |
|---|---|---|---|---|---|
| Crude extract | 1263.4 | 273.7 | 0.22 | 100 | 1 |
| Heat precipitation | 345.9 | 114.3 | 0.33 | 41.7 | 1.5 |
| $Ni^{2+}$-NTA | 3.1 | 3.1 | 0.38 | 1.13 | 1.7 |
| Gel filtration | 0.015 | 0.32 | 20.9 | 0.18 | 95 |

The determination of protein concentrations was performed according to Bradford (1976, Anal Biochem 72: 248-254). For this purpose, 1 ml of Bradford reagent (0.007% (w/v) Serva Blau G-250, 5% (v/v) of ethanol, 8.5% (v/v) of $H_3PO_4$) was mixed with 10 μl of the protein sample and incubated at room temperature for 5 minutes. The absorbance was determined at the wavelength λ=595 nm by spectrophotometry. Bovine serum albumin (BSA) in concentrations of 0.1-1.0 mg/ml was used for preparing calibration lines.

Example 6

Determination of the Molecular Weight of FgXyl3A

The determination of the molecular weight of FgXyl3A was performed by means of denaturing and native polyacryl amide gel electrophoresis.

The denaturing separation of proteins was performed by means of sodium dodecyl sulfate polyacrylamide gel electrophoresis (SDS-PAGE) according to Laemmli (1970, Nature 227 (5259): 680-685). "Unstained Protein Molecular Weight Marker" or, respectively, "PageRuler™ Unstained Protein Ladder" by Fermentas (St. Leon-Rot) was used as the protein standard. The gel run was carried out in a "Minuteni-Protean Tetra" system (Bio-Rad, Munich) in 25 mM of tris, 192 mM of glycine, 0.1% (w/v) SDS at constant 200 V. The gels were incubated for 30 minutes in Coomassie dye solution (0.25% (w/v) Serva Blau G-250, 45% (v/v) ethanol, 10% (v/v) acetic acid) and then decoloured in a decolouring solution (30% (v/v) ethanol, 10% (v/v) acetic acid). The gels were incubated in a drying solution (20% (v/v) ethanol, 2% (v/v) glycerine) for 10 minutes for the purpose of preservation and dried with the aid of the "DryEase® Minuteni-Gel Drying System" (Invitrogen, Karlsruhe).

The determination of the molecular weight of native proteins and native protein complexes was performed by native polyacryl amide gel electrophoresis. 4-12% (w/v) tris-glycine gradient gels (Anamed Electrophorese, Groβ-Bieberau) were used for this purpose. Before the run, native sample buffer (7.5% (v/v) glycerine, 0.04% (w/v) of bromophenol blue, 33 mM tris, pH 6.8) was added to the protein sample. "High Molecular Weight-Marker (GE Healthcare, Munich) served as the protein standard. The gel run was performed in a "Novex® XCell II™ Minuteni-Cell" facility (Invitrogen, Karlsruhe) for 3 hrs at constant 120 V in 25 mM tris and 192 mM glycine. The gels were incubated in Coomassie dye solution, decoloured and dried for preservation.

Figure 4:
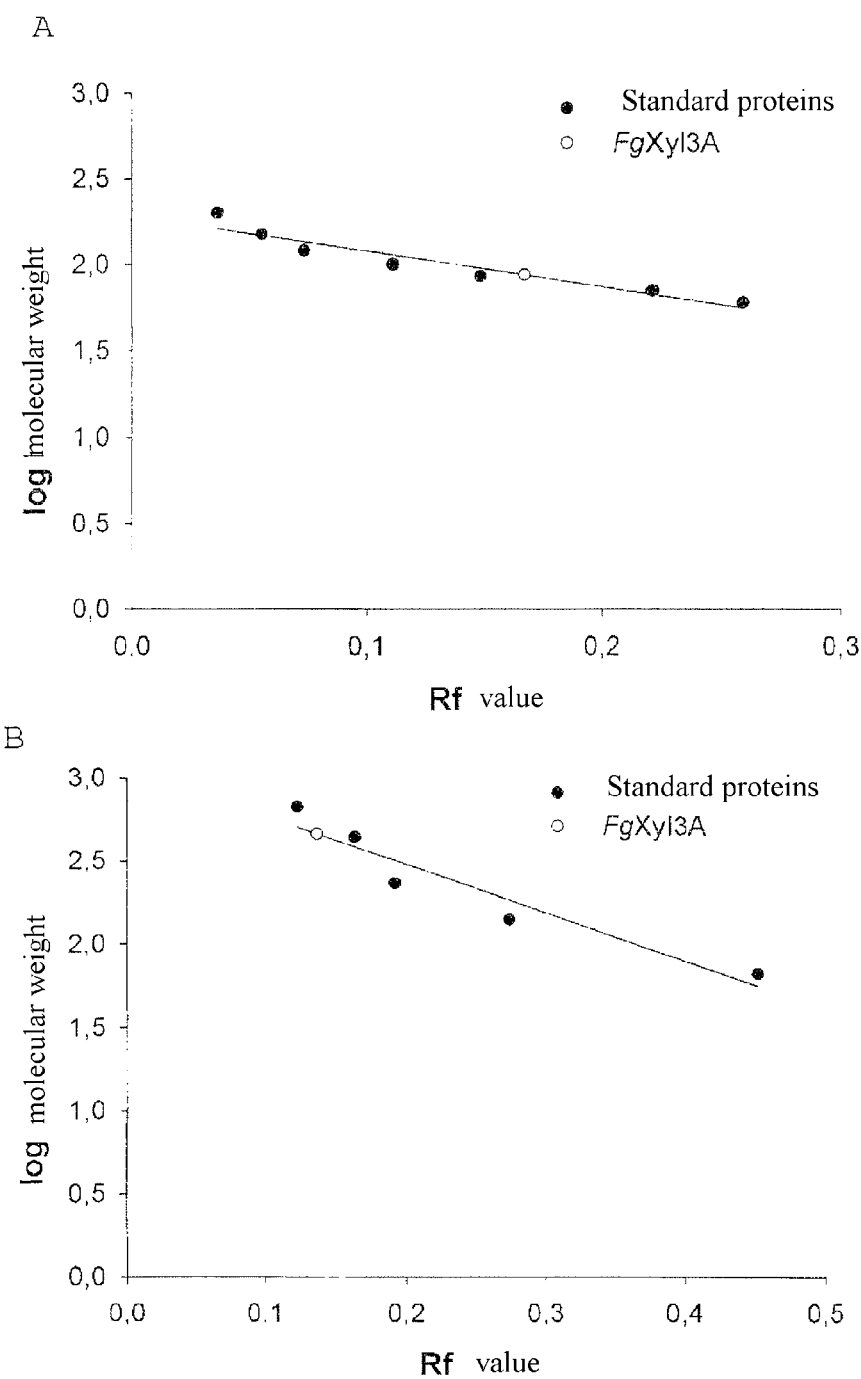

Under denaturing conditions, the recombinant protein had a molecular weight of 87 kDa (FIG. 4 A). Under native conditions, a molecular weight of 529.7 kDa was determined (FIG. 4 B). This indicates that the protein FgXyl3A might be present as a homohexamer.

Example 7

Detection of the Activity of FgXyl3A in SDS Gels

The detection of enzymatic activity with the aid of zymograms was performed after the electrophoretic separation of the proteins by SDS-PAGE (example 6). After the run, the gels were incubated in 1% (v/v) Triton X 100 at room temperature (RT) for 1 hr. The β-xylosidase activity of FgXyl3A was detected by incubation of the gels in 0.1% (w/v) esculin, 0.01% (w/v) ammonium iron(III) citrate and 50 mM Na-acetate (pH 6.0) for 30-60 minutes at 60° C.

Example 8

Examination of the Enzymatic Activity of FgXyl3A

For the determination of the substrate spectrum of FgXyl3A, the activity of the purified recombinant proteins (example 5) vis-à-vis pNP-β-D-galactopyranoside, pNP-α-D-glucopyranoside, pNP-β-D-glucopyranoside, pNP-β-D-cellobioside and pNP-β-D-xylopyranoside was examined. The substrates were used in a final concentration of 2 mM and the activities were measured by the following standard tests.

(1) Determination of the β-glucosidase activity: The activity of the β-glucosidase was determined in a modified manner according to Park et al. (2005, Appl. Microbiol. Biotechnol. 69 (4): 411-422) using pNP-β-D-glucopyranoside (Sigma-Aldrich, Munich) as the substrate. Unless otherwise indicated, a reaction sample contained 2 mM pNP-β-D-glucopyranoside and 50 mM Na-acetate (pH 6.0) in an overall volume of 1 ml. Before adding 0.02 U of the enzyme, the reaction samples were incubated at 80° C. for 5 minutes. The reactions were performed at 80° C. for 10 minutes and then stopped by adding 100 µl of 0.1 M Na$_2$CO$_3$ and placing the sample on ice. All the measurements were taken in the form of triple determinations. The enzyme was added to the control batches only after Na$_2$CO$_3$ had been added and incubation on ice performed. The determination of the released p-nitrophenol was performed at a wavelength of λ=410 nm. The enzymatic activity was calculated by the following formula:

$$\text{Enzymatic activity (U/ml)} = (\Delta E \cdot V_{Tot})/(d \cdot e \cdot t \cdot V_E)$$

ΔE is defined as the change in extinction, $V_{Tot}$ as the reaction volume (ml), d as the thickness of the cuvette (cm), e as the molar extinction coefficient (M$^{-1}$ cm$^{-1}$), t as the reaction time (minutes) and $V_E$ as the volume of the enzyme sample (ml). 16.56 M-1 cm-1 is used as the molar extinction coefficient. 1 U β-glucosidase activity was defined as the amount of enzyme which releases 1 µmol of p-nitrophenol per minute under standard conditions.

(2) Determination of the β-xylosidase activity: pNP-β-D-Xylopyranoside (Sigma-Aldrich, Munich) was used as the substrate for determining the activity of β-xylosidase in the modified form according to Park et al. (2005, Appl. Microbiol. Biotechnol. 69 (4): 411-422). Unless otherwise described, the standard reaction to determine the β-xylosidase activity was carried out in the presence of 2 mM pNP-β-D-xylopyranoside and 50 mM Na-acetate (pH 6.5) in a total volume of 1 ml. The reactions were started by adding 0.016 U enzyme to the batches pre-incubated at 85° C. for five minutes and then carried out at a temperature of 85° C. for 10 minutes. The reactions were stopped by adding 100 µl 0.1 M Na$_2$CO$_3$ and placing the samples on ice. All the measurements were taken in the form of triple determinations. Reaction samples to which the enzyme was added only after addition of Na$_2$CO$_3$ and incubation on ice served as controls. The spectrophotometric measurement of the released p-nitrophenols was performed at a wavelength of λ=410 nm. The enzymatic activity was calculated by the following formula:

$$\text{Enzymatic activity (U/ml)} = (\Delta E \cdot V_{tot})/(d \cdot e \cdot t \cdot V_E)$$

ΔE is defined as the change in extinction, $V_{Tot}$ as the reaction volume (ml), d as the thickness of the cuvette (cm), e as the molar extinction coefficient (M$^{-1}$ cm$^{-1}$), t as the reaction time (minutes) and $V_E$ as the volume of the enzyme sample (ml). 16.56 M-1 cm-1 was used as the molar extinction coefficient. 1 U β-xylosidase activity was defined as the amount of enzyme which led to a release of 1 µmol of p-nitrophenol per minute under standard conditions.

FgXyl3A showed the highest specific activity with 20.9 U/mg vis-à-vis pNP-β-xylopyranoside (Table 2). In addition, a specific activity of 1.3 and, respectively 9.3 U/mg vis-à-vis pNP-α- and pNP-β-glucopyranoside was determined. The substrate pNP-β-galactopyranoside was also hydrolysed by the β-xylosidase, the specific activity being 2.7 U/mg. Hydrolysis of the disaccharide pNP-β-cellobioside by Xyl3A was not detected (Table 2).

TABLE 2

Substrate specificity of FgXyl3A

| Substrate | Specific activity [U/mg] |
|---|---|
| pNP-β-xylopyranoside | 20.9 |
| pNP-β-glucopyranoside | 9.3 |
| pNP-α-glucopyranoside | 1.3 |
| pNP-β-galactopyranoside | 2.7 |
| pNP-β-cellobioside | 0 |

Example 9

Influence of the Temperature on the Activity of FgXyl3A

For determination of the temperature profile of FgXyl3A, the enzymatic activity of the recombinant proteins (example 5) was measured in a temperature range of 10-115° C. with pNP-β-xylopyranoside as the substrate as described in example 8. For this purpose, the reaction batches were pre-incubated at the relevant temperature for 5 minutes before adding the enzyme. Activity was determined by the standard test (example 8).

Figure 5:
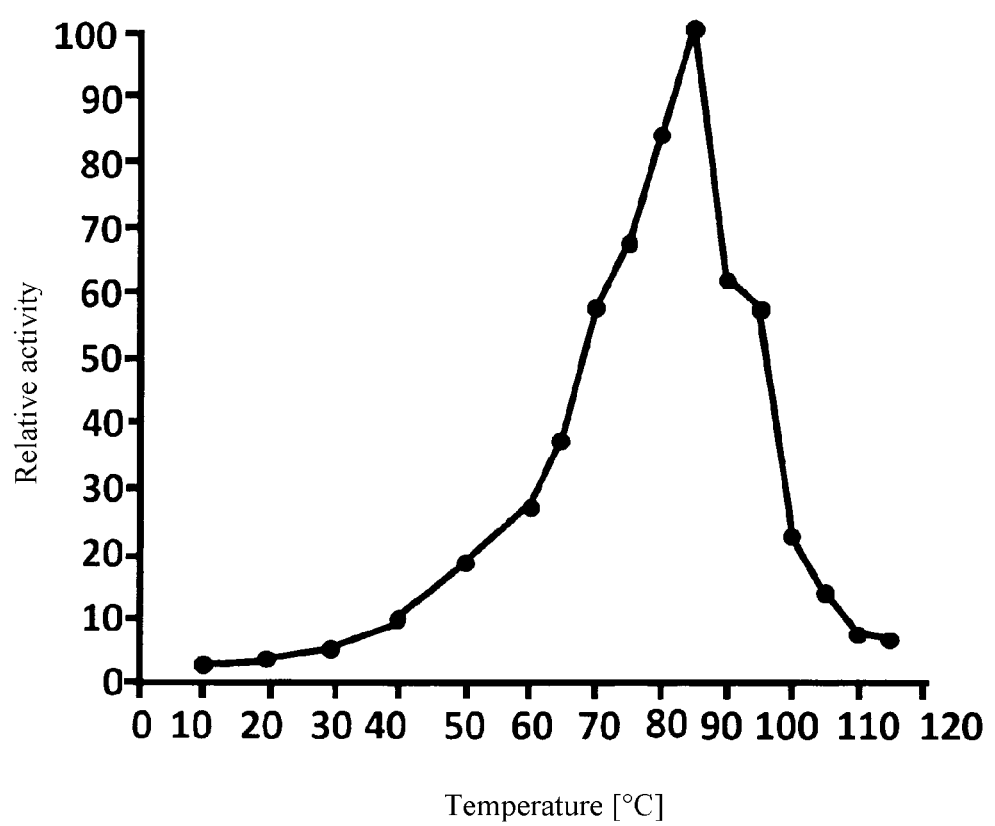

FgXyl3A showed β-xylosidase activity in a wide temperature range (FIG. 5). More than 50% of the relative activity was measured at temperatures of 70-95° C., maximum activity being measured at 85° C. A pronounced decrease in activity was observed at temperatures above 95° C.; for example, the activity of FgXyl3A at 100° C. was 23% of the maximum activity. 18-38% of the relative activity was measured in a temperature range of 50-65° C.

Example 10

Temperature Stability of FgXyl3A

For the determination of temperature stability, recombinant FgXyl3A (example 5) was incubated at temperatures of 60-90° C. for up to 24 hrs. The residual activity was determined under standard conditions (example 8).

Figure 6:
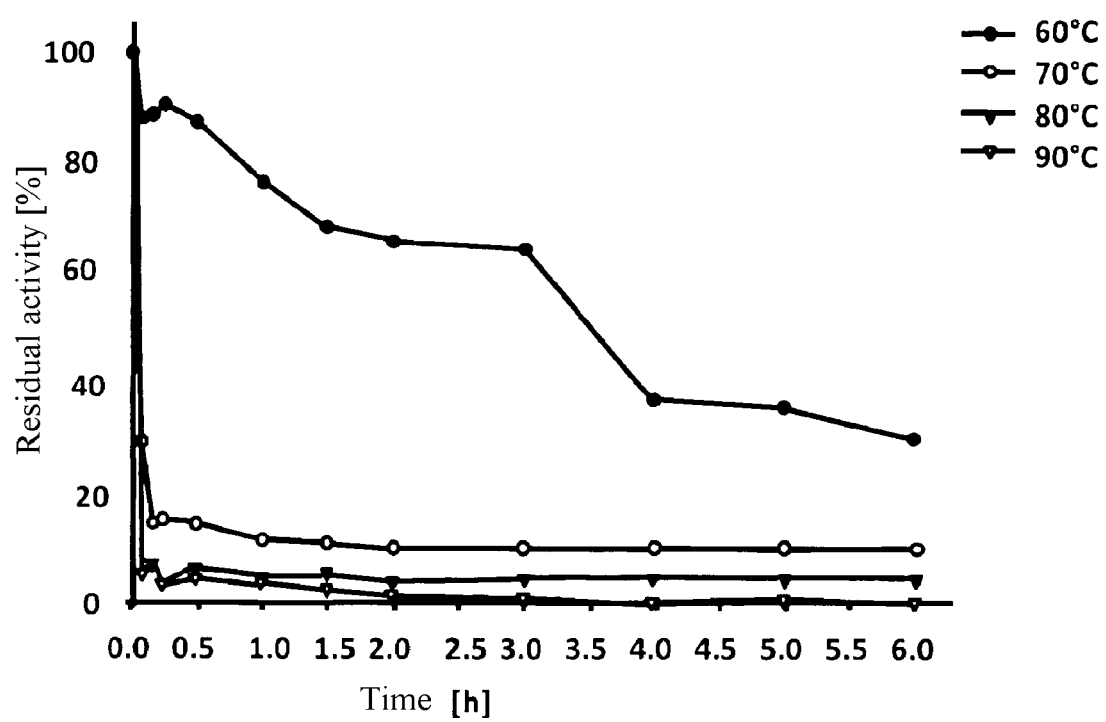

Measured by the residual β-xylosidase activity, FgXyl3A was stable for a period of 3 hours at a temperature of 60° C. Incubation at 70-90° C., on the other hand, caused deactivation of the enzyme after a few minutes (FIG. 6). By pre-incubation of FgXyl3A at 60° C., 65% of residual activity was determined after 2 hrs; after 6 hrs of incubation the activity was 30%. After a longer incubation of 24 hrs, the enzyme exhibited a residual activity of 25%. At a temperature of 70° C., FgXyl3A exhibited 30% of residual activity after 5 minutes of incubation; and 15% residual activity after 10 minutes of pre-incubation. The half-life of FgXyl3A was 215 minutes at 60° C. and 6 minutes at 70° C.

Example 11

Influence of the pH-Value on the Activity of FgXyl3A

Figure 7:
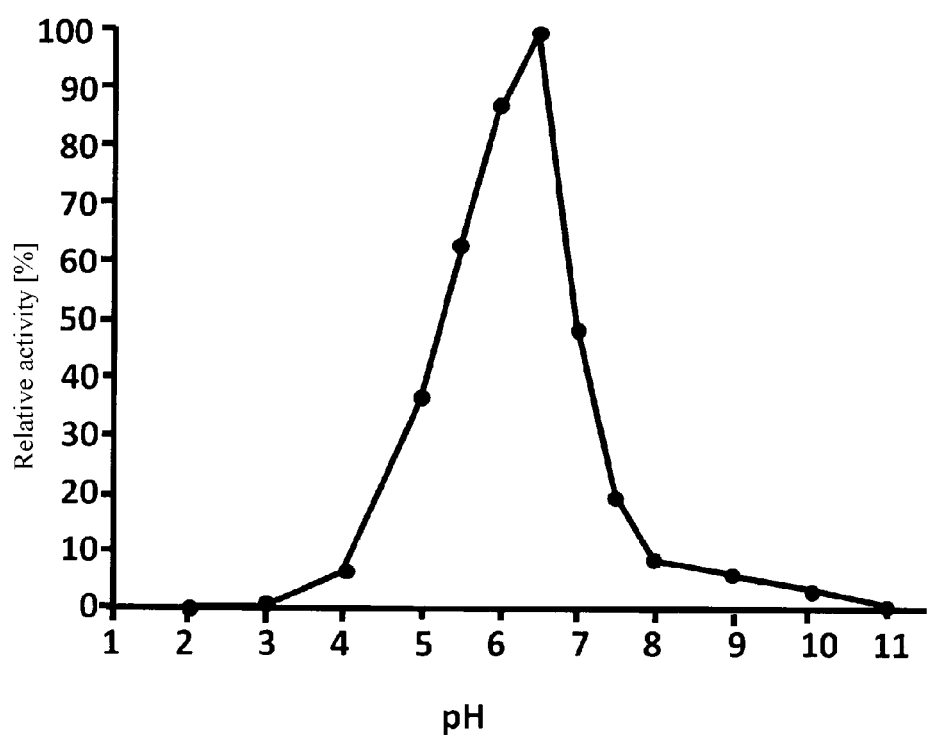

For the determination of the pH profile of FgXyl3A, the activity of the recombinant enzyme (example 5) in a pH range of 2.0-11.0 with pNP-β-xylopyranoside as the substrate was measured (example 8). The reactions were carried out in the presence of 50 mM of universal buffer (16.7 mM $H_3PO_4$, 16.7 mM of acetic acid, 16.7 mM of $H_3BO_4$, Britton & Robinson, 1931) under standard conditions (example 8). The maximum activity of FgXyl3A vis-àvis β-xylosidase was measured at a pH value of 6.5 (FIG. 7). In the pH range of 5.5-7.0, the β-xylosidase exhibited more than 45% of the relative activity, a pronounced decrease in activity being observed at pH values above 7.0. In the acidic pH range, the enzyme did not exhibit any activity at pH 2.0-3.0 and at pH 4.0 exhibited a maximum activity of 6%. A relative activity of 36% was measured at pH 5.0.

Example 12

Determination of the pH Stability of FgXyl3A

For determination of the pH stability, recombinant FgXyl3A (example 5) was incubated in 50 mM of universal buffer with pH-values of 3.0-10.0 for 48 hrs at room temperature. This was followed by the determination of the residual activity under standard conditions (example 8), but in the presence of 50 mM of universal buffer having a pH-value of 6.5.

Figure 8:
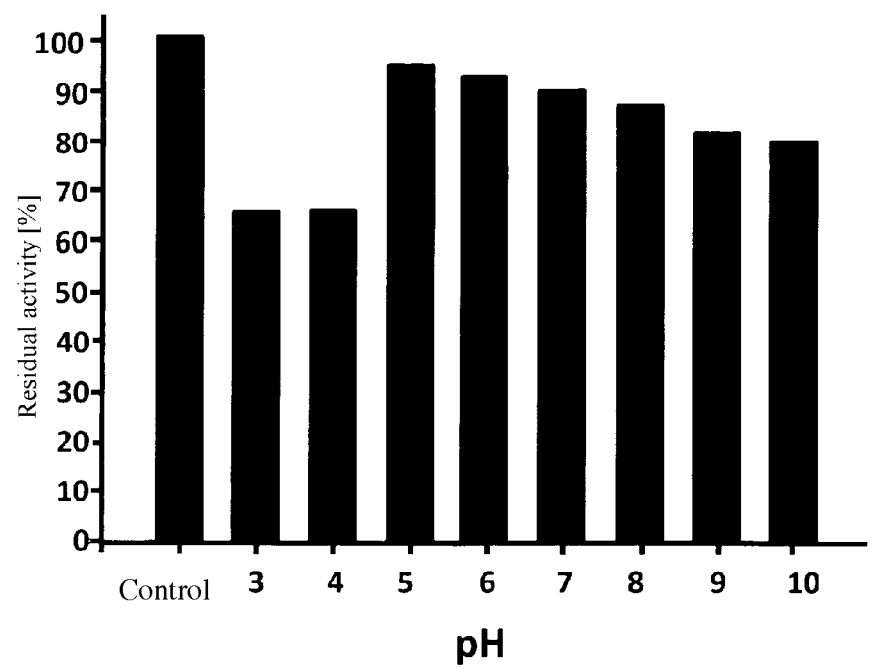

In the slightly acidic and neutral pH range of 5.0-7.0, FgXyl3A exhibited high stability with a residual activity vis-àvis β-xylosidase of 90-95% (FIG. 8). In the acidic pH range, on the other hand, a loss in activity was observed. For example, the residual activity was 66% at pH 3.0 and 4.0. A small loss in activity was observed in the alkaline pH range, where residual activity of 87% was measured at pH 8.0, 81% at pH 9.0 and 80% at pH 10.0.

Example 13

Product Analysis by High-Performance Liquid Chromatography (HPLC)

For detection of the hydrolysis products formed, 0.5% (w/v) of beech wood xylan, xylobiose, xylotriose and xylotetraose were incubated in 50 mM $NaH_2PO_4$ (pH 6.5) with 0.1 U β-xylosidase for up to 3 hrs at 80° C. The samples were boiled for 10 minutes to stop the reaction and then centrifuged for 10 minutes at 13000×g and 4° C. The supernatants of the samples were filtered (0.2 μm pore size, Pall, Darmstadt) and transferred into sample bottles with micro-inserts (CS Chromatographie Service, Langerwehe). 20 μl of each sample was injected. The analysis of the products was performed using an Aminex HPX 42-A column (Bio-Rad, Munich), using degassed $H_2O$ (LiCrosolv®, Merck, Darmstadt) as the mobile phase and selecting a flow rate of 0.6 ml/minute at a temperature of 70° C.

Figure 9:
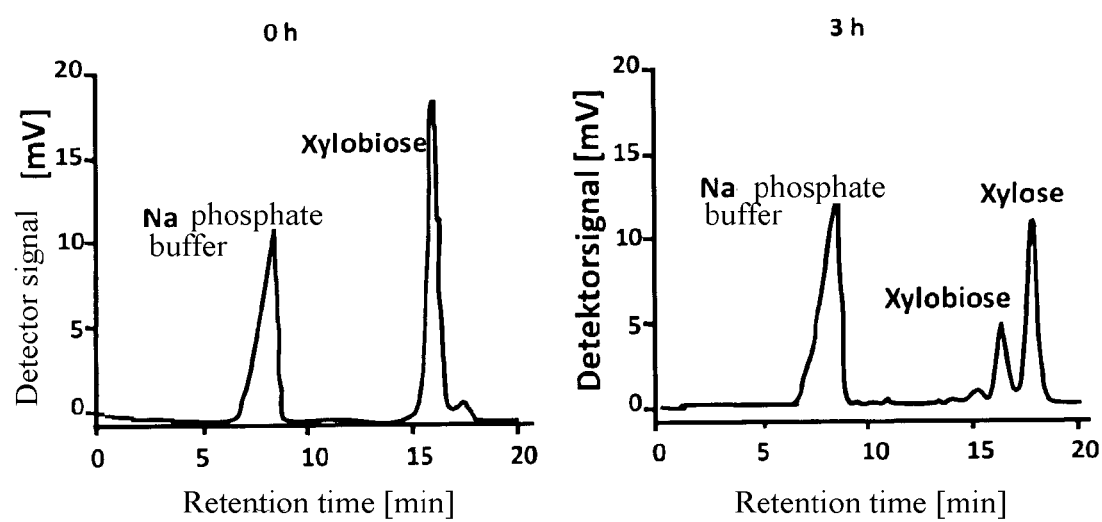
Figure 10:
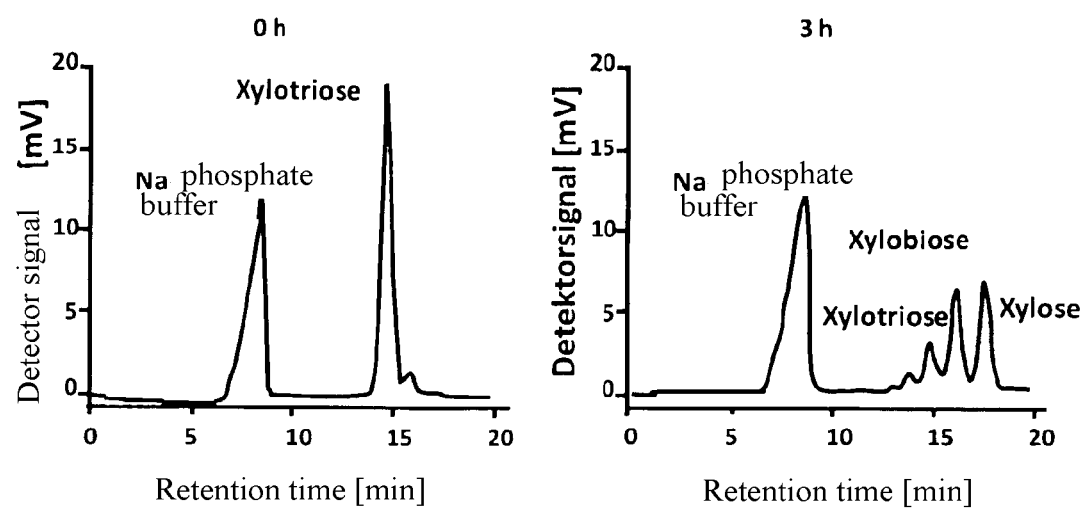
Figure 11:
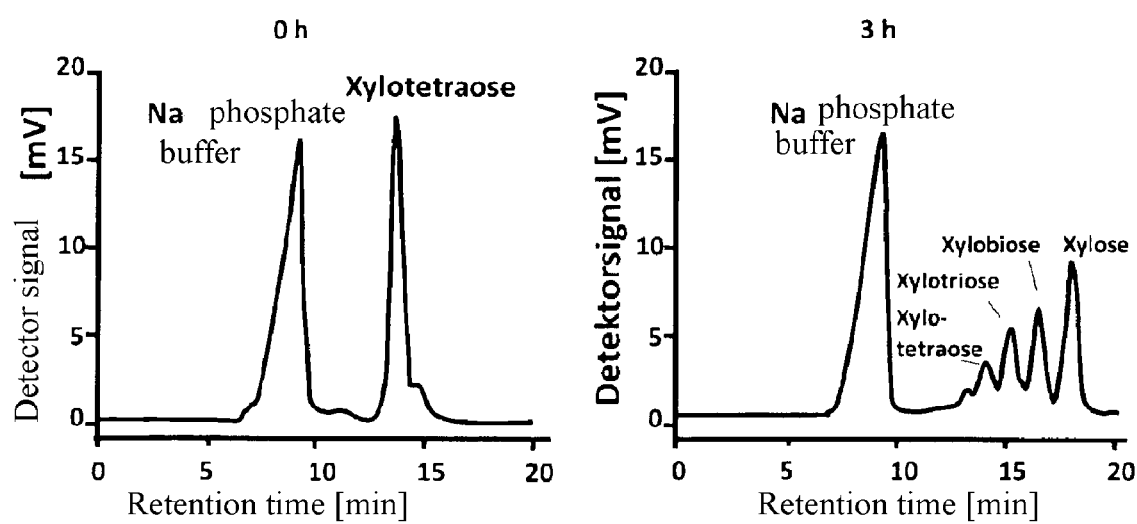

After incubation of the enzyme for 3 hrs in the presence of xylobiose, a major part of the substrate was hydrolysed to form xylose (FIG. 9). The incubation of FgXyl3A with xylotriose resulted in the formation of xylose and xylobiose, a large proportion part of the substrates being hydrolysed (FIG. 10). If FgXyl3A was incubated with the substrate xylotetraose, the hydrolysis products xylose, xylobiose and xylotriose were detected, xylose being the main product (FIG. 11). Longer incubation did not result in an increased degradation of xylotetraose. If the FgXyl3A was incubated in the presence of beech wood xylan, small amounts of xylose were detected as the hydrolysis product.

Example 14

Kinetics of FgXyl3A

Figure 12:
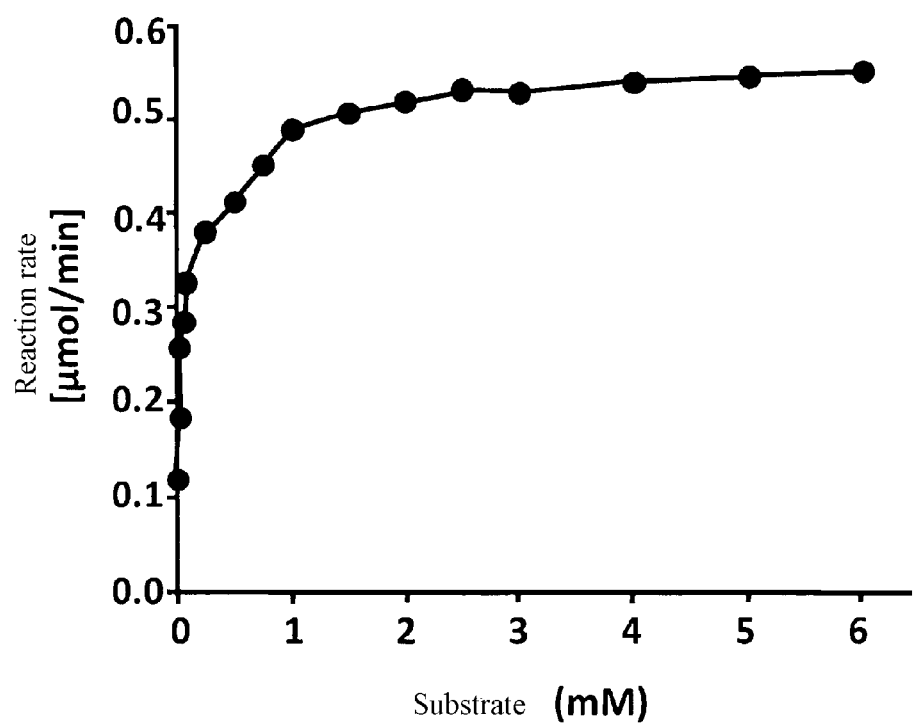

The determination of the kinetic parameters of the β-xylosidase activity of FgXyl3A was performed at substrate concentrations of 0.01-6.0 mM pNP-β-D-xylopyranoside. The reaction was performed under standard conditions (example 8). The determination of $v_{max}$ and $K_M$ was done by non-linear regression according to Michaelis-Menten and yielded a $v_{max}$ value of 0.53 μmol/min and a $K_M$ value of 0.06 mM (FIG. 12).

Overview of the Sequences in the Sequence Listing:
SEQ ID NO. 1: FgXyl3A full-length protein
SEQ ID NO. 2: catalytic domain GHF 3 from SEQ ID NO. 1 (corresponds to amino acid residues 13 to 638 of SEQ ID NO. 1)
SEQ ID NO. 3: DNA sequence encoding SEQ ID NO. 1
SEQ ID NO. 4: barley β-D-glucan-exohydrolase isoenzyme Exo I, full length

SHORT DESCRIPTION OF THE DRAWINGS

FIG. 1: Domain structure of FgXyl3A

FIG. 1 shows the domain structure β-xylosidase FgXyl3A determined by means of "InterProScan". GHF: glycoside hydrolase family.

Figure 2:
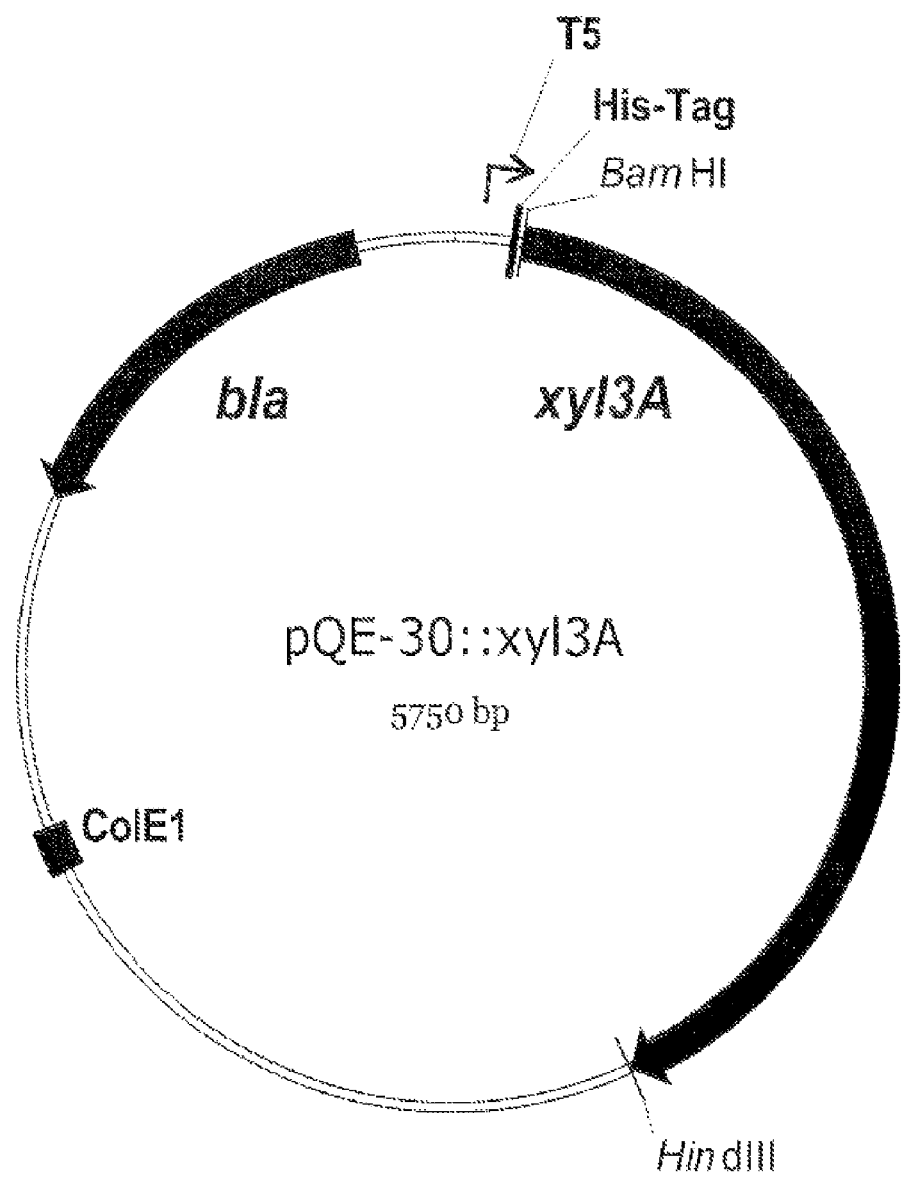

FIG. 2: Vector map of the recombinant plasmid pQE-30::xyl3A

The xyl3A gene encoding the β-xylosidase FgXyl3A gene was ligated into the expression vector pQE-30 using the restriction cleavage sites BamHI and HindIII. T5: T5 promoter, bla: β-lactamase, ColE1: replication origin.

FIG. 3: Purification and detection of the activity of FgXyl3A

The purification and activity of FgXyl3A was detected by means of SDS-PAGE. The proteins were dyed with Coomassie-Blau; the activity of FgXyl3A was detected by esculin. Track 1: Protein standard "PageRuler™ Unstained Protein Ladder" (Fermentas, St. Leon-Rot), Track 2: Crude extract of E. coli M15/pQE-30 (control, 35 μg), track 3: crude extract of E. coli M15/pQE-30::xyl3A (37 μg), track 4: heat-precipitated crude extract of E. coli M15/pQE-30::xy/3A (35 μf), track 5: Ni$^{2+}$-NTA fraction of FgXyl3A (40 μg), track 6: gel filtration fraction of FgXyl3A (1.1 μg), track 7: activity gel of the gel filtration fraction of FgXyl3A (1.1 μg).

FIG. 4: Determination of the molecular weight of FgXyl3A

The molecular weight of FgXyl3A was determined by means of denaturing and native polyacryl amide gel electrophoresis. In the Figure the logarithm of the molecular weight is plotted against the running distance of the proteins in the gel (Rf value). Molecular weights of the standard proteins in (A): Recombinant proteins having a size of 200, 150, 120, 100, 85, 70 and 60 kDa. Molecular weights of the standard proteins in (B): thyroglobulin (669 kDa), ferritin (440 kDa), catalase (232 kDa), lactate dehydrogenase (140 kDa), albumin (66 kDa).

FIG. 5: Temperature profile of FgXyl3A

The activity of FgXyl3A was determined in a temperature range of 10-115° C. under standard conditions. Reaction parameters: 2 mM pNP-β-xylopyranoside, 50 mM Na-acetate, pH 6.5; 10 mM incubation time.

FIG. 6: Temperature stability of FgXyl3A

The temperature stability of FgXyl3A was determined after pre-incubation of the enzyme at temperatures of 60-100° C. Reaction parameters: 2 mM pNP-β-xylopyranoside, 50 mM Na-acetate, pH 6.5, 85° C.; 10 min incubation time.

FIG. 7: pH-Profile of FgXyl3A

The activity of FgXyl3A was determined in a pH range of 2.0-11.0 under standard conditions. Reaction parameters: 2 mM pNP-β-xylopyranoside, 50 mM universal buffer, 85° C.; 10 mM incubation time.

FIG. 8: pH Stability of FgXyl3A

The pH stability of FgXyl3A was determined after pre-incubation of the enzyme at pH values of 3.0-10.0 under standard conditions. Reaction parameters: 2 mM pNP-β-xylopyranoside, 50 mM universal buffer, 85° C.; 10 minutes incubation time.

FIG. 9: Hydrolysis of xylobiose by FgXyl3A

The hydrolysis products were analysed after incubation of FgXyl3A for 3 hrs in the presence of 0.5% (w/v) xylobiose, 20 mM Na-phosphate buffer, pH 6.5, 80° C. by HPLC.

FIG. 10: Hydrolysis of xylotriose by FgXyl3A

The hydrolysis products were analysed after incubation of FgXyl3A for 3 hrs in the presence of 0.5% (w/v) xylotriose, 20 mM Na-phosphate buffer, pH 6.5, 80° C. by HPLC.

FIG. 11: Hydrolysis of xylotetraose by FgXyl3A

The hydrolysis products were analysed after incubation of FgXyl3A for 3 hrs in the presence of 0.5% (w/v) xylotetraose, 20 mM Na-phosphate buffer, pH 6.5, 80° C. by HPLC.

FIG. 12: Kinetics of FgXyl3A

The figure shows the Michaelis-Menten plot of FgXyl3A. The activity of FgXyl3A was determined under standard conditions. Reaction parameters: 0.01-6.0 mM of pNP-β-xylopyranoside, 50 mM of Na-acetate, pH 6.5, 85° C.; 10 minutes incubation time.

The invention claimed is:

1. A fusion protein, said fusion protein comprising:
a first polypeptide and
a second polypeptide,
said first polypeptide comprising:
an amino acid sequence having at least 90% sequence identity with SEQ ID NO. 2, and a catalytic domain capable of hydrolysing a β-glycosidic bond on a pyranose;
wherein said first polypeptide is a recombinant polypeptide having β-pyranosidase activity;
wherein said β-pyranosidase activity is thermostable in the temperature range of 60-100° C.; and
wherein said second polypeptide is at least one of a signal peptide, an affinity tag, or a protease cleavage site.

2. The fusion protein according to claim 1, wherein the β-pyranosidase activity is β-xylopyranosidase activity, β-glucopyranosidase activity or a combination of these two activities.

3. The fusion protein according to claim 1, wherein said first polypeptide is capable of hydrolysing a β-glycosidic bond on a xylose.

4. The fusion protein according to claim 1, wherein said first polypeptide is capable of hydrolysing at least one of the β-glycoside bonds contained in a substrate, wherein said substrate is at least one of xylobiose, xylotriose, xylotetraose, or xylan.

5. The fusion protein of claim 1 wherein the pNP-β-cellobioside activity of said first polypeptide is 5% or less compared with the pNP-β-xylobioside activity of said first polypeptide wherein such activity is determined for each of pNP-β-cellobioside and pNP-β-xylobioside by incubating 0.01-6.0 mM at 60-90° C., in about 50 mM universal buffer at a pH of 5-7 for 5 to 30 minutes.

6. A vector containing a nucleic acid, said nucleic acid encoding a polypeptide said polypeptide comprising:
an amino acid sequence having at least 90% sequence identity with SEQ ID NO. 2, and a catalytic domain capable of hydrolysing a β-glycosidic bond on a pyranose;
wherein said polypeptide is a recombinant polypeptide having β-pyranosidase activity;
wherein said β-pyranosidase activity is thermostable in the temperature range of 60-100° C.

7. A host cell transformed with a vector according to claim 6.

8. The host cell according to claim 7, said host cell being an eukaryote selected from the group consisting of *Saccharomyces cerevisiae, Yarrowia lipolytica, Schizosaccharomyces lactis, Kluyveromyces lactis, Pichia methanolytica, Pichia pastoris, Pichia angusta, Hansenula polymorpha, Aspergillus niger, Chrysosporium lucknowense, -Trichoderma reesei,* and *Penicillium* sp.

9. The host cell according to claim 7, said host cell being a methylotrophic yeast selected from the group consisting of *Pichia methanolytica, Pichia pastoris, Pichia angusta,* and *Hansenula polymorpha.*

10. The host cell according to claim 7, said host cell being a prokaryote selected from the group consisting of *Bacillus* sp., *Bacillus subtilis, Bacillus licheniformis; Bacillus megaterium, Thermus thermophilus, Pseudomonas fluorescens, Fervidobacterium* sp., and *Escherichia coli.*

11. The host cell according to claim 7, said host cell being a *Bacillus subtilis.*

* * * * *

SEQUENCE LISTING

```
<160> NUMBER OF SEQ ID NOS: 4

<210> SEQ ID NO 1
<211> LENGTH: 775
<212> TYPE: PRT
<213> ORGANISM: Fervidobacterium gondwanense

<400> SEQUENCE: 1

Met Glu Ile Tyr Lys Asp Ser Ser Lys Pro Ile Glu Leu Arg Val Glu
1               5                   10                  15

Asp Leu Leu Ser Arg Met Thr Leu Glu Glu Lys Val Ser Gln Leu Gly
```

```
            20                  25                  30
Ser Val Trp Ser Tyr Gln Leu Leu Asp Glu Asn Gly Asn Phe Asp Glu
            35                  40                  45
Gly Lys Ala Phe Glu Leu Leu Lys Asp Gly Ile Gly Gln Ile Ser Arg
 50                  55                  60
Pro Gly Gly Ala Thr Asn Phe Gln Pro Glu Val Ala Gln Phe Asp
 65                  70                  75                  80
Asn Lys Val Gln Lys Phe Leu Ile Glu Asn Thr Arg Leu Gly Ile Pro
            85                  90                  95
Ala Leu Met His Glu Glu Cys Leu Thr Gly Tyr Met Gly Leu Asn Gly
            100                 105                 110
Ser Asn Phe Pro Val Pro Ile Ala Met Ala Ser Thr Trp Glu Pro Glu
            115                 120                 125
Leu Val Lys Glu Val Thr Lys Val Ile Arg Gln Glu Met Arg Asn Met
 130                 135                 140
Gly Ile His Gln Gly Leu Ala Pro Val Leu Asp Val Ala Arg Asp Pro
 145                 150                 155                 160
Arg Trp Gly Arg Val Glu Glu Thr Phe Gly Glu Ser Pro Tyr Leu Val
                 165                 170                 175
Ala Ser Met Gly Cys Ala Tyr Val Glu Gly Leu Gln Gly Glu Asp Leu
             180                 185                 190
Lys Asp Gly Val Ile Ala Thr Thr Lys His Phe Val Gly Tyr Ser Ala
             195                 200                 205
Ser Glu Gly Gly Arg Asn Trp Ala Pro Thr Asn Ile Pro Pro Arg Glu
         210                 215                 220
Leu Arg Glu Ile Phe Met Phe Pro Phe Glu Ala Ala Val Lys Val Ala
 225                 230                 235                 240
Lys Val Gly Ser Val Met Asn Ser Tyr Ser Glu Ile Asp Gly Val Pro
                 245                 250                 255
Leu Ala Ala Ser Arg Glu Leu Leu Thr Asp Val Leu Arg Lys Glu Trp
             260                 265                 270
Gly Phe Asp Gly Leu Val Val Ser Asp Tyr Phe Ser Val Lys Leu Ile
         275                 280                 285
His Glu His His Lys Leu Ala Arg Asp Lys Ala Glu Ala Ala Lys Tyr
 290                 295                 300
Ala Leu Glu Ala Gly Ile Asp Val Glu Leu Pro Asn Thr Asp Cys Tyr
 305                 310                 315                 320
Ala His Val Leu Asp Leu Val Lys Ser Gly Val Ile Pro Glu Lys Leu
                 325                 330                 335
Leu Asp Gln Thr Val Arg Arg Ile Leu Lys Met Lys Phe Lys Leu Gly
             340                 345                 350
Leu Phe Asp Lys Pro Tyr Val Glu Pro Ser Lys Ala Lys Val Val Lys
         355                 360                 365
Asn Thr Glu Leu Ala Leu Glu Val Ala Arg Lys Ser Ile Val Leu Leu
 370                 375                 380
Lys Asn Asp Gly Ile Leu Pro Leu Lys Lys Asp Met Lys Val Ala Leu
 385                 390                 395                 400
Ile Gly Pro Asn Ala Ala Asp Val Arg Asn Met Leu Gly Asp Tyr Met
                 405                 410                 415
Tyr Leu Ala His Ile Lys Ile Met Leu Glu Asn Val Asn Leu Ala Phe
             420                 425                 430
Asp Ala Pro Lys Phe Asn Leu Ser Ser Val Lys Lys Ser Val Glu Glu
         435                 440                 445
```

```
Ser Met Asn Lys Ile Lys Ser Ile Glu Met Leu Leu Lys Glu Glu Ser
    450                 455                 460

Val Gln Phe Thr Tyr Ala Lys Gly Cys Asp Val Leu Gly Asp Ser Lys
465                 470                 475                 480

Glu Gly Phe Asn Glu Ala Leu Lys Ala Val Glu Asn Ser Asp Val Ala
                485                 490                 495

Ile Val Val Val Gly Asp Arg Ser Gly Leu Thr Met Asp Cys Thr Thr
            500                 505                 510

Gly Glu Ser Arg Asp Ser Ala Asn Leu Lys Leu Pro Gly Val Gln Glu
        515                 520                 525

Glu Leu Ile Ile Glu Val Ser Lys Val Gly Lys Pro Val Val Leu Ala
    530                 535                 540

Leu Leu Asn Gly Arg Pro Tyr Ser Leu Thr Arg Val Val Asp Lys Val
545                 550                 555                 560

Ser Ala Ile Val Glu Ala Trp Leu Pro Gly Glu Ile Gly Ala Lys Ala
                565                 570                 575

Ile Val Asp Val Leu Tyr Gly Lys Val Asn Pro Ser Gly Lys Leu Pro
            580                 585                 590

Met Thr Phe Pro Arg Ser Ala Gly Gln Ile Pro Leu Phe His Tyr Phe
        595                 600                 605

Lys Pro Ser Gly Gly Arg Ser Ser Trp His Gly Asp Tyr Val Asp Glu
    610                 615                 620

Ser Val Lys Pro Leu Phe Pro Phe Gly His Gly Leu Ser Tyr Thr Asn
625                 630                 635                 640

Phe Asp Tyr Ser Gly Leu Glu Ile Ser Pro Ser Lys Val Pro Met Ala
                645                 650                 655

Gly Ser Val Glu Ile Ser Leu Tyr Val Glu Asn Thr Gly Glu Val Glu
            660                 665                 670

Gly Glu Glu Val Val Gln Leu Tyr Ile Gly Arg Glu Cys Ala Ser Val
        675                 680                 685

Thr Arg Pro Val Lys Glu Leu Lys Gly Phe Ala Lys Val Asn Leu Lys
    690                 695                 700

Pro Gly Glu Lys Arg Lys Val Leu Phe Asn Leu His Thr Asp Val Leu
705                 710                 715                 720

Ala Phe Tyr Gly Arg Asp Met Lys Leu Cys Val Glu Pro Gly Val Tyr
                725                 730                 735

Asn Val Met Ile Gly Ser Ser Asp Asp Ile Arg Leu Lys Gly Ser
            740                 745                 750

Phe Glu Val Asp Gly Met Arg Arg Glu Val Phe Glu Asp Arg Val Phe
        755                 760                 765

Phe Thr Lys Val Tyr Thr Phe
    770                 775

<210> SEQ ID NO 2
<211> LENGTH: 625
<212> TYPE: PRT
<213> ORGANISM: artificial
<220> FEATURE:
<223> OTHER INFORMATION: segment consisting of amino acid residues 13 to
      638 of SEQ ID NO 1

<400> SEQUENCE: 2

Arg Val Glu Asp Leu Leu Ser Arg Met Thr Leu Glu Glu Lys Val Ser
1               5                   10                  15

Gln Leu Gly Ser Val Trp Ser Tyr Gln Leu Leu Asp Glu Asn Gly Asn
```

```
            20                  25                  30
Phe Asp Glu Gly Lys Ala Phe Glu Leu Leu Lys Asp Gly Ile Gly Gln
            35                  40                  45
Ile Ser Arg Pro Gly Gly Ala Thr Asn Phe Gln Pro Glu Glu Val Ala
 50                  55                  60
Gln Phe Asp Asn Lys Val Gln Lys Phe Leu Ile Glu Asn Thr Arg Leu
 65                  70                  75                  80
Gly Ile Pro Ala Leu Met His Glu Glu Cys Leu Thr Gly Tyr Met Gly
                85                  90                  95
Leu Asn Gly Ser Asn Phe Pro Val Pro Ile Ala Met Ala Ser Thr Trp
                100                 105                 110
Glu Pro Glu Leu Val Lys Glu Val Thr Lys Val Ile Arg Gln Glu Met
            115                 120                 125
Arg Asn Met Gly Ile His Gln Gly Leu Ala Pro Val Leu Asp Val Ala
            130                 135                 140
Arg Asp Pro Arg Trp Gly Arg Val Glu Thr Phe Gly Glu Ser Pro
145                 150                 155                 160
Tyr Leu Val Ala Ser Met Gly Cys Ala Tyr Val Glu Gly Leu Gln Gly
                165                 170                 175
Glu Asp Leu Lys Asp Gly Val Ile Ala Thr Thr Lys His Phe Val Gly
                180                 185                 190
Tyr Ser Ala Ser Glu Gly Gly Arg Asn Trp Ala Pro Thr Asn Ile Pro
            195                 200                 205
Pro Arg Glu Leu Arg Glu Ile Phe Met Phe Pro Phe Glu Ala Ala Val
            210                 215                 220
Lys Val Ala Lys Val Gly Ser Val Met Asn Ser Tyr Ser Glu Ile Asp
225                 230                 235                 240
Gly Val Pro Leu Ala Ala Ser Arg Glu Leu Leu Thr Asp Val Leu Arg
                245                 250                 255
Lys Glu Trp Gly Phe Asp Gly Leu Val Val Ser Asp Tyr Phe Ser Val
                260                 265                 270
Lys Leu Ile His Glu His His Lys Leu Ala Arg Asp Lys Ala Glu Ala
            275                 280                 285
Ala Lys Tyr Ala Leu Glu Ala Gly Ile Asp Val Glu Leu Pro Asn Thr
            290                 295                 300
Asp Cys Tyr Ala His Val Leu Asp Leu Val Lys Ser Gly Val Ile Pro
305                 310                 315                 320
Glu Lys Leu Leu Asp Gln Thr Val Arg Arg Ile Leu Lys Met Lys Phe
                325                 330                 335
Lys Leu Gly Leu Phe Asp Lys Pro Tyr Val Glu Pro Ser Lys Ala Lys
                340                 345                 350
Val Val Lys Asn Thr Glu Leu Ala Leu Glu Val Ala Arg Lys Ser Ile
            355                 360                 365
Val Leu Leu Lys Asn Asp Gly Ile Leu Pro Leu Lys Lys Asp Met Lys
            370                 375                 380
Val Ala Leu Ile Gly Pro Asn Ala Ala Asp Val Arg Asn Met Leu Gly
385                 390                 395                 400
Asp Tyr Met Tyr Leu Ala His Ile Lys Ile Met Leu Glu Asn Val Asn
                405                 410                 415
Leu Ala Phe Asp Ala Pro Lys Phe Asn Leu Ser Ser Val Lys Lys Ser
            420                 425                 430
Val Glu Glu Ser Met Asn Lys Ile Lys Ser Ile Glu Met Leu Leu Lys
            435                 440                 445
```

Glu Glu Ser Val Gln Phe Thr Tyr Ala Lys Gly Cys Asp Val Leu Gly
    450                 455                 460

Asp Ser Lys Glu Gly Phe Asn Glu Ala Leu Lys Ala Val Glu Asn Ser
465                 470                 475                 480

Asp Val Ala Ile Val Val Gly Asp Arg Ser Gly Leu Thr Met Asp
                485                 490                 495

Cys Thr Thr Gly Glu Ser Arg Asp Ser Ala Asn Leu Lys Leu Pro Gly
                500                 505                 510

Val Gln Glu Glu Leu Ile Ile Glu Val Ser Lys Val Gly Lys Pro Val
        515                 520                 525

Val Leu Ala Leu Leu Asn Gly Arg Pro Tyr Ser Leu Thr Arg Val Val
    530                 535                 540

Asp Lys Val Ser Ala Ile Val Glu Ala Trp Leu Pro Gly Glu Ile Gly
545                 550                 555                 560

Ala Lys Ala Ile Val Asp Val Leu Tyr Gly Lys Val Asn Pro Ser Gly
                565                 570                 575

Lys Leu Pro Met Thr Phe Pro Arg Ser Ala Gly Gln Ile Pro Leu Phe
                580                 585                 590

His Tyr Phe Lys Pro Ser Gly Gly Arg Ser Ser Trp His Gly Asp Tyr
            595                 600                 605

Val Asp Glu Ser Val Lys Pro Leu Phe Pro Phe Gly His Gly Leu Ser
    610                 615                 620

Tyr
625

<210> SEQ ID NO 3
<211> LENGTH: 2328
<212> TYPE: DNA
<213> ORGANISM: Fervidobacterium gondwanense

<400> SEQUENCE: 3
atggagatat ataaggattc ttctaagcct attgaattga gagttgagga cctgctttcg      60
agaatgacgc tggaagaaaa ggttagccag ctcggttctg tttggagtta tcaattactc     120
gacgagaacg ggaatttcga tgaagggaaa gcatttgagc tgttgaagga cggcataggt     180
caaatctcaa gaccgggtgg agcaacaaac tttcaacccg aagaagttgc tcaattcgac     240
aataaagtac agaaattctt gatagaaaat acgagacttg aataccagc attaatgcac     300 gaagaatgcc taactggata tatgggactc aacggttcga attttcctgt gcctatcgcg     360
atggcgagta cgtgggagcc tgaactggta aggaagtta cgaaagtgat aaggcaagag     420
atgaggaata tgggaattca ccaagggctc gctcctgtac ttgacgttgc aagggaccca     480
agatggggaa gggttgagga acattcgga gagtcgcctt atcttgtcgc aagtatgggg     540
tgtgcttatg tcgaaggtct gcagggagaa gacttgaaag acggagtcat tgccactaca     600
aagcactttg tcggttacag cgcgtctgaa ggagggcgga actgggctcc aactaacatt     660
ccgccacgcg agttgagaga tcttcatg ttcccattcg aagctgccgt gaaagtagcg     720
aaggttggtt ctgttatgaa ttcgtacagc gagatagacg gagtgcctct tgccgcctcc     780
agagagcttt taacagatgt gctgaggaaa gaatgggat tgatggact cgttgtctct     840 gattatttct cggtgaagtt gatccacgaa catcacaaat agcaaggga taaagccgaa     900 gcagcaaaat acgcccttga agcgggaata gatgtgaat accaaatac cgattgctat     960 gcacatgtct tagacctggt gaaaagcggg gttattccgg aaaagttgtt agatcaaact    1020

```
gttagaagga ttttgaagat gaaatttaaa ttgggcttgt tcgataagcc gtacgtagaa    1080
ccttcaaaag cgaaggttgt aaaaaacaca gagcttgctc ttgaagttgc aagaaagtca    1140
atagtgctcc ttaagaacga cggtatcttg ccattgaaaa aagatatgaa agtagcactc    1200
ataggaccaa atgcggcgga tgtcaggaac atgctcggtg attacatgta cttagcacat    1260
ataaaaataa tgctcgagaa cgttaacttg gcttttgatg cgcctaagtt caatctttca    1320
agcgtgaaga aatcggttga ggagagcatg aacaagatca agagtataga gatgttgctc    1380
aaagaagaaa gtgttcaatt cacatacgcg aaaggttgcg atgtcttggg agattcgaaa    1440
gaagggttca acgaggcgct caaagcagtc gagaatagcg atgtggcgat agttgtagtt    1500
ggtgataggt caggtttgac catggattgc acaacgggtg agtcgaggga cagcgcgaat    1560
ttgaagttgc ccggagttca ggaagaactt atcattgagg tttcaaaggt tggcaagcct    1620
gtggtgctcg ctttgctgaa tggcagacct tattctttaa ccagggttgt agacaaggtt    1680
tctgctattg ttgaggcgtg gttgccaggt gagattggtg caaaggcaat agtcgatgtg    1740
ctttacggca aagtcaatcc atccggtaaa cttccaatga ctttcccgag aagtgctggt    1800
cagattccgc tcttccacta cttcaaaccg tctggcggaa ggtccagttg gcatggtgac    1860
tacgttgacg agagtgtcaa accactattc ccgttcggtc acggactttc gtatactaat    1920
ttcgattaca gcgggttaga aatctctcca tcaaaagtgc caatggcagg aagcgtcgaa    1980
atttcacttt atgtggagaa cactggtgaa gttgaaggcg aagaggttgt gcagctttac    2040
atcggaagag aatgtgcctc agtaactcgg ccagttaagg aactgaaagg ttttgcgaag    2100
gtgaatttga aacctggcga aaagaggaaa gttttgttca atctccacac ggacgtgctc    2160
gcgttctacg gacgcgatat gaagctctgc gttgagcctg ggtttacaa cgtcatgatt    2220 ggaagttctt cggatgatat aaggcttaaa ggaagttttg aggtagatgg aatgagaaga    2280
gaggtatttg aagatagagt attctttaca aaagtttaca ctttctaa               2328
```

```
<210> SEQ ID NO 4
<211> LENGTH: 630
<212> TYPE: PRT
<213> ORGANISM: Hordeum vulgare
<300> PUBLICATION INFORMATION:
<301> AUTHORS: Varghese et al.
<303> JOURNAL: Structure
<304> VOLUME: 7
<305> ISSUE: 2
<306> PAGES: 179-190
<307> DATE: 1999

<400> SEQUENCE: 4

Met Ala Leu Leu Thr Ala Pro Ala Val Phe Ala Ala Leu Leu Leu Phe
1               5                   10                  15

Trp Ala Val Leu Gly Gly Thr Asp Ala Asp Tyr Val Leu Tyr Lys Asp
            20                  25                  30

Ala Thr Lys Pro Val Glu Asp Arg Val Ala Asp Leu Leu Gly Arg Met
        35                  40                  45

Thr Leu Ala Glu Lys Ile Gly Gln Met Thr Gln Ile Glu Arg Leu Val
    50                  55                  60

Ala Thr Pro Asp Val Leu Arg Asp Asn Phe Ile Gly Ser Leu Leu Ser
65                  70                  75                  80

Gly Gly Gly Ser Val Pro Arg Lys Gly Ala Thr Ala Lys Glu Trp Gln
                85                  90                  95

Asp Met Val Asp Gly Phe Gln Lys Ala Cys Met Ser Thr Arg Leu Gly
            100                 105                 110
```

```
Ile Pro Met Ile Tyr Gly Ile Asp Ala Val His Gly Gln Asn Asn Val
            115                 120                 125

Tyr Gly Ala Thr Ile Phe Pro His Asn Val Gly Leu Gly Ala Thr Arg
130                 135                 140

Asp Pro Tyr Leu Val Lys Arg Ile Gly Glu Ala Thr Ala Leu Glu Val
145                 150                 155                 160

Arg Ala Thr Gly Ile Gln Tyr Ala Phe Ala Pro Cys Ile Ala Val Cys
                165                 170                 175

Arg Asp Pro Arg Trp Gly Arg Cys Tyr Glu Ser Tyr Ser Glu Asp Arg
            180                 185                 190

Arg Ile Val Gln Ser Met Thr Glu Leu Ile Pro Gly Leu Gln Gly Asp
        195                 200                 205

Val Pro Lys Asp Phe Thr Ser Gly Met Pro Phe Val Ala Gly Lys Asn
    210                 215                 220

Lys Val Ala Ala Cys Ala Lys His Phe Val Gly Asp Gly Gly Thr Val
225                 230                 235                 240

Asp Gly Ile Asn Glu Asn Asn Thr Ile Ile Asn Arg Glu Gly Leu Met
                245                 250                 255

Asn Ile His Met Pro Ala Tyr Lys Asn Ala Met Asp Lys Gly Val Ser
            260                 265                 270

Thr Val Met Ile Ser Tyr Ser Ser Trp Asn Gly Val Lys Met His Ala
        275                 280                 285

Asn Gln Asp Leu Val Thr Gly Tyr Leu Lys Asp Thr Leu Lys Phe Lys
    290                 295                 300

Gly Phe Val Ile Ser Asp Trp Glu Gly Ile Asp Arg Ile Thr Thr Pro
305                 310                 315                 320

Ala Gly Ser Asp Tyr Ser Tyr Ser Val Lys Ala Ser Ile Leu Ala Gly
                325                 330                 335

Leu Asp Met Ile Met Val Pro Asn Asn Tyr Gln Gln Phe Ile Ser Ile
            340                 345                 350

Leu Thr Gly His Val Asn Gly Gly Val Ile Pro Met Ser Arg Ile Asp
        355                 360                 365

Asp Ala Val Thr Arg Ile Leu Arg Val Lys Phe Thr Met Gly Leu Phe
    370                 375                 380

Glu Asn Pro Tyr Ala Asp Pro Ala Met Ala Glu Gln Leu Gly Lys Gln
385                 390                 395                 400

Glu His Arg Asp Leu Ala Arg Glu Ala Ala Arg Lys Ser Leu Val Leu
                405                 410                 415

Leu Lys Asn Gly Lys Thr Ser Thr Asp Ala Pro Leu Leu Pro Leu Pro
            420                 425                 430

Lys Lys Ala Pro Lys Ile Leu Val Ala Gly Ser His Ala Asp Asn Leu
        435                 440                 445

Gly Tyr Gln Cys Gly Gly Trp Thr Ile Glu Trp Gln Gly Asp Thr Gly
    450                 455                 460

Arg Thr Thr Val Gly Thr Thr Ile Leu Glu Ala Val Lys Ala Ala Val
465                 470                 475                 480

Asp Pro Ser Thr Val Val Phe Ala Glu Asn Pro Asp Ala Glu Phe
                485                 490                 495

Val Lys Ser Gly Gly Phe Ser Tyr Ala Ile Val Ala Val Gly Glu His
            500                 505                 510

Pro Tyr Thr Glu Thr Lys Gly Asp Asn Leu Asn Leu Thr Ile Pro Glu
        515                 520                 525
```

-continued

```
Pro Gly Leu Ser Thr Val Gln Ala Val Cys Gly Gly Val Arg Cys Ala
    530             535             540
Thr Val Leu Ile Ser Gly Arg Pro Val Val Gln Pro Leu Leu Ala
545             550             555             560
Ala Ser Asp Ala Leu Val Ala Ala Trp Leu Pro Gly Ser Glu Gly Gln
            565             570             575
Gly Val Thr Asp Ala Leu Phe Gly Asp Phe Gly Phe Thr Gly Arg Leu
            580             585             590
Pro Arg Thr Trp Phe Lys Ser Val Asp Gln Leu Pro Met Asn Val Gly
        595             600             605
Asp Ala His Tyr Asp Pro Leu Phe Arg Leu Gly Tyr Gly Leu Thr Thr
    610             615             620
Asn Ala Thr Lys Lys Tyr
625             630
```